United States Patent
Abdolahad et al.

(10) Patent No.: US 9,851,343 B2
(45) Date of Patent: Dec. 26, 2017

(54) ELECTRICAL CELL-SUBSTRATE IMPEDANCE SENSOR (ECIS)

(71) Applicants: Mohammad Abdolahad, Tehran (IR); Milad Gharooni, Tehran (IR); Shamsoddin Mohajerzadeh, Tehran (IR); Hamed Abiri, Tehran (IR); Mohsen Janmaleki, Tehran (IR)

(72) Inventors: Mohammad Abdolahad, Tehran (IR); Milad Gharooni, Tehran (IR); Shamsoddin Mohajerzadeh, Tehran (IR); Hamed Abiri, Tehran (IR); Mohsen Janmaleki, Tehran (IR)

( * ) Notice: Subject to any disclaimer, the term of this patent is extended or adjusted under 35 U.S.C. 154(b) by 0 days.

(21) Appl. No.: 15/058,922

(22) Filed: Mar. 2, 2016

(65) Prior Publication Data
US 2016/0178613 A1   Jun. 23, 2016

Related U.S. Application Data

(60) Provisional application No. 62/127,803, filed on Mar. 3, 2015.

(51) Int. Cl.
| | |
|---|---|
| *C12Q 1/02* | (2006.01) |
| *G01N 33/483* | (2006.01) |
| *H01L 21/02* | (2006.01) |
| *G01N 27/02* | (2006.01) |
| *G01N 33/50* | (2006.01) |
| *G01N 33/574* | (2006.01) |
| *G01N 27/327* | (2006.01) |

(52) U.S. Cl.
CPC ......... *G01N 33/4836* (2013.01); *G01N 27/02* (2013.01); *G01N 27/021* (2013.01); *G01N 27/3278* (2013.01); *G01N 33/5011* (2013.01); *G01N 33/5044* (2013.01); *G01N 33/574* (2013.01); *H01L 21/02381* (2013.01); *H01L 21/02488* (2013.01); *H01L 21/02532* (2013.01); *H01L 21/02603* (2013.01); *H01L 21/02645* (2013.01); *H01L 21/02653* (2013.01)

(58) Field of Classification Search
None
See application file for complete search history.

(56) References Cited

U.S. PATENT DOCUMENTS

| 8,022,444 | B2 * | 9/2011 | Kim .................. G01N 27/4146 257/255 |
| 2004/0152067 | A1 | 8/2004 | Wang |
| 2007/0172939 | A1 | 7/2007 | Xu |

OTHER PUBLICATIONS

ATCC website, http://www.atcc.org/Products/Cells_and_Microorganisms/By_Disease_Model/Cancer/Source_Tissue.aspx> Feb. 4, 2014 (Accessed Nov. 2, 2016).*
Sigma (<http://www.sigmaaldrich.com/europe/life-science-offers/cell-cycle/sigma-ecacc-cel> Dec. 28, 2014 (Accessed Nov. 1, 2016).*
Pradhan et al., RSC Adv., 4:9432-9438 (2014).*
Alexander et al., Analyst, 137, 5823-5828 (2012).*
Ravindran et al., IEEE, ECT Conf., 1015-1020 (2010).*
Nguyen et al., Anal. Chem., 85:11068-11076 (2013).*
Wolf et al., Thermochimica Acta, 337:27-38 (1999).*
Hong et al., Analyst, 136:237-245 (2011).*
Tossi et al., J. Med. Phys., 39(3):192-196 (2014).*
Yang et al., Anal. Bioanal. Chem., 399:1823-1833 (2011).*
Wegener et al., Exp. Cell Res., 259:158-166 (2000).*
Kim et al., Nanoscale Res. Lett., 8(502):1-7 (2013).*
Martinez et al., Nano Let., 9(3):1121-1126 (2009).*
Rashid et al., J. Biomater., pp. 1-16 (2013).*
Yan et al., Electrochimica Acta, 61:148-153 (2012).*
Misra et al., PNAS, 106(33):13780-13784 (2009).*
Abdolahad et al., Lab Chip, 12:1183-1190 (2012).*
PCT/IB2016/051107 Declaration of Non-Establishment of International Search Report and Written Opinion dated May 30, 2016.
Mohammad Abdolahad, Silicon nanograss based impedance biosensor for label free detection of rare metastic cells among primary cancerous colon cells, suitable for more accurate cancer staging, Biosensors and Bioelectronics, vol. 59, Sep. 15, 2014, pp. 151-159.
Woong Kim, Interfacing Silicon Nanowires with Mammalian Cells, Journal of the American Chemical Society, vol. 129, Issue 23, May 22, 2007, pp. 7228-7229.
Zhiqiang Gao, Silicon Nanowire Arrays for Label-Free Detection of DNA, Analytical Chemistry, vol. 79, Issue 9, Apr. 4, 2007, pp. 3291-3297.
Mohammad Abdolahad, Cell membrane electrical charge investigations by silicon nanowires incorporated field effect transistor (SiNWFET) suitable in cancer research, RSC Advances, vol. 4, Nov. 22, 2013, pp. 7425-7431.

* cited by examiner

*Primary Examiner* — Thomas J Visone
(74) *Attorney, Agent, or Firm* — NovoTechIP International PLLC

(57) ABSTRACT

A method for detection and monitoring a therapeutic effect of a cancer treatment drug is disclosed. The method includes steps of removing a malignant biological cell lines from a tumor; culturing the removed biological cell lines in a controlled set of conditions; seeding the cultured biological cell lines on silicon nanowire electrode arrays of an electrical cell-substrate impedance sensor (ECIS); adding a cancer treatment drug to the seeded biological cell lines to treat the seeded biological cell lines; and measuring an electrical impedance of the treated biological cell lines for detection and monitoring a therapeutic effect of the cancer treatment drug.

27 Claims, 39 Drawing Sheets

ELECTRICAL CELL-SUBSTRATE IMPEDANCE SENSOR (ECIS)

CROSS REFERENCE TO RELATED APPLICATION

The present application claims priority from U.S. Provisional Patent Application Ser. No. 62/127,803, filed Mar. 3, 2015, entitled "A Biosensor for Monitoring the Spreading Stage of the Cells and Applications thereof for Cancer Diagnosis", which is incorporated by reference herein in its entirety.

TECHNICAL FIELD

The present application generally relates to a device including a silicon nanowire based electrical cell impedance sensor (designated hereinafter as "SiNW-ECIS") and a method for fabrication of a SiNW-ECIS. Moreover, the use of a SiNW-ECIS as a biosensor for detecting the electrical response of cultured living cells, specifically cancerous cells is disclosed.

BACKGROUND

The cancer cells are different from healthy cells in reproduction, adhesion, proliferation rate, maturation and function (specialization), which all might affect the electrical and chemical signals recorded from the cell. Biologists introduce the cancer as a disease, characterized by the autonomous aimless and excessive proliferation of cells.

The growing cycle of the biological cells includes three main phases. The three main phases include (i) attachment to a substrate, (ii) spreading or stretching of cell until splitting, and (iii) proliferation or mitosis. The spreading stage, as one of the important pre-proliferation stages, may contain many distinguishable parameters between normal and malignant cells. In addition, the effect of anti-cancer drugs may be distinguishable at the spreading stage. The spreading stage may occur about 10 hours before the proliferation stage. Therefore, it may be advantageous to determine the cancerous state of the cell during the spreading stage and also determine the anti-cancer drug effects during the spreading stage. However, the impedimetric monitoring of the spreading stage in normal and cancerous cells has not been carried out for diagnosis applications to date.

Hence, there is a need for fabrication of cancer cells ECIS biosensors with the ability to diagnose the cancer cells at their spreading stage for a faster response.

SUMMARY

In one general aspect of the present application, an electrical cell substrate impedance sensor (ECIS) for measuring an electrical response of a biological cell is disclosed. The ECIS includes a substrate, a catalyst layer formed on the substrate; and a plurality of nanowire electrodes array grown on the catalyst layer, the plurality of nanowire electrodes are configured to measure an electrical response of a biological cell.

The above general aspect may include one or more of the following features. The substrate may include a silicon dioxide ($SiO_2$) layer grown on a silicon chip or a silicon wafer. The catalyst layer may include a nanometer sized layer of gold or a bilayer of Ni—Au. The nanowire electrodes may include a plurality of silicon nanowires (SiNWs) having a thickness less than 100 nanometers.

In another general aspect of the present application, a method for fabricating a silicon nanowire based electrical cell substrate impedance sensor (SiNW-ECIS) is described. The method includes the steps of: growing a layer of silicon dioxide (SiO2) on a silicon chip or a silicon wafer, as the substrate layer, using a wet oxidation furnace or chamber; forming a catalyst layer on the substrate layer via a sputtering technique; etching the catalyst layer in a region corresponding to the sensor region on the substrate through a photolithography process; growing a plurality of silicon nanowire (SiNW) arrays configured to measure an electrical response of a biological cell on the sensor region to form a SiNW-ECIS; and transferring the SiNW-ECIS into a doping furnace The above general method aspect may include one or more of the following features. The doping furnace may include a phosphorous doping furnace to enhance the electrical conductivity of nanowires. Furthermore, a device for measuring the electrical response or impedance of a biological cell line may be presented in the present application. The device may include a sensor package including SiNW-ECIS, a system for applying and acquiring the electrical signals and data to the biological cell lines attached on the ECIS silicon nanowires placed within the sensor package, and a data processor to record and process the acquired data.

In another general aspect of the present application, a method for detecting and monitoring the spreading stage of a biological cell for cancer diagnosis is disclosed. The method includes steps of: removing biological cell lines from a normal tissue or a cancerous tumor; culturing the removed biological cell lines via maintaining in a controlled set of conditions; seeding the cultured biological cells lines on silicon nanowire electrode arrays of a SiNW-ECIS described above; and measuring an electrical impedance of the seeded biological cell lines to detect and monitor a spreading state of the seeded biological cell lines for cancer diagnosis.

In another general aspect of the present application, a method for detecting and monitoring the therapeutic effects of specific cancer treatment drugs is disclosed. The electrical response of the cancerous cells treated by low concentrations of specific drugs, particularly, antitubulin drugs is recorded after short time intervals of drug incubation. The method is carried out using the SiNW-ECIS and the measuring device including the SiNW-ECIS, designed and fabricated pursuant to the teachings of the present application.

In one implementation, the method for detecting and monitoring the therapeutic effects of cancer treatment drugs includes the steps of: removing a malignant biological cell lines from a tumor; culturing the removed biological cell lines in a controlled set of conditions; seeding the cultured biological cell lines on silicon nanowire electrode arrays of an electrical cell-substrate impedance sensor (ECIS); adding a treatment drug to the seeded biological cell lines to treat the seeded biological cell lines; and measuring an electrical impedance of the treated biological cell lines for detection and monitoring the therapeutic effect of a specific cancer treatment drug, particularly, antitubulin drugs.

In another implementation, cell lines culturing in both methods mentioned hereinabove for cancer diagnosis and monitoring the therapeutic effects of cancer drugs may be achieved by maintaining the cell lines in a controlled set of conditions including maintaining the cell lines in a medium, particularly, RPMI-1640 medium and in a $CO_2$ incubator at a specific temperature.

In another implementation, seeding the cultured biological cell lines in both methods mentioned hereinabove for cancer diagnosis and monitoring the therapeutic effects of cancer drugs may include: dropping the cultured biological cell lines on a surface of a packed and sealed ECIS; and maintaining the dropped biological cell lines in an incubator to achieve attachment between the biological cell lines and the silicon nanowire electrode arrays of ECIS. The treatment drug addition may include: first, adding a specific amount of the treatment drug on a surface of the biological cell lines attached on the silicon nanowire electrode arrays, and second, maintaining the biological cell lines with the added treatment drug in an incubator for a specific time interval.

Furthermore, measuring the electrical impedance in both methods mentioned hereinabove for cancer diagnosis and monitoring the therapeutic effects of cancer drugs may include measuring the electrical impedance via the device disclosed in the present application including: applying a specific voltage of about 400 mV to the sensor package having the biological cells attached to the silicon nanowire electrode arrays, and measuring the electrical impedance of the biological cells attached to the silicon nanowire electrode arrays at various specific frequencies in a range of about 100 Hz to 150 KHz.

DETAILED DESCRIPTION

Figure 1A:
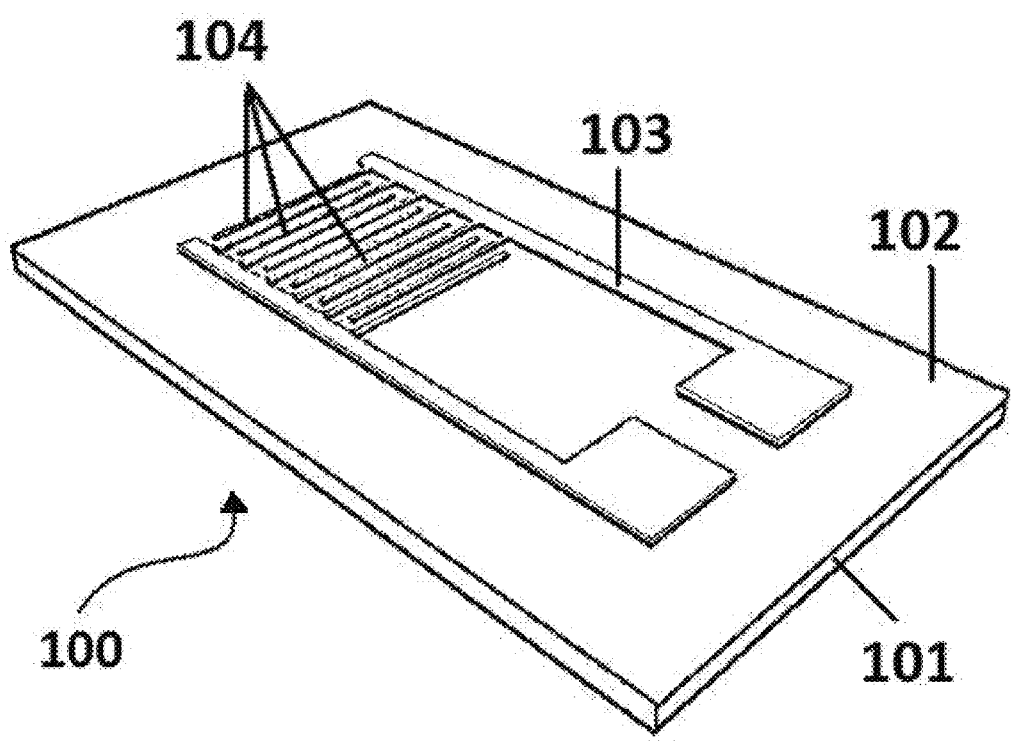
FIG. 1A illustrates a schematic of an exemplary SiNW-ECIS fabricated pursuant to the teachings of the present application.

The following detailed description is presented to enable a person skilled in the art to make and use the application. For purposes of explanation, specific nomenclature is set forth to provide a thorough understanding of the present application. However, it will be apparent to one skilled in the art that these specific details are not required to practice the teachings of the present application. Descriptions of specific applications are provided only as representative examples. Various modifications to the implementations discussed in the present application will be readily apparent to one skilled in the art, and the general principles defined herein may be applied to other implementations and applications without departing from the scope of the present application. The present application is not intended to be limited to the implementations shown, but is to be accorded the widest possible scope consistent with the principles and features disclosed herein.

Nanostructured materials, as nanoscale interactors, have suitable bioelectrical properties, leading to a development of a new generation of nanostructured-based ECIS. Electrically active nanomaterials could have well-directed electrical interaction with cell outer-wall to penetrate the electric field into the cell membrane for signal recording purposes. Among various nanomaterials applied in bio-sensing processes, silicon nanowires (SiNWs) have found a wide range of applications in the field of bioelectronics. This is because SiNWs have unique chemical and physical properties and may be compatible with the fabrication process of electronic devices.

To this end, the present application describes a device including a silicon nanowire-based electrical cell impedance sensor (SiNW-ECIS) and the fabrication method thereof. The SiNW-ECIS may have a simple fabrication and testing process and may be considered for label-free cancer detection methods, especially when large amount of cells are required to be checked.

The SiNW-ECIS is a biosensor that monitors the spreading stage of biological cells. The spreading stage may include a stage at which the biological cells stretch and become extended on the nanowires surface. The SiNW-ECIS is configured to detect the cancerous state of cultured living cells by monitoring the spreading stage of the biological cells. Additionally, the SiNW-ECIS is configured to investigate the effect of anti-cancer drugs via monitoring their interruption effects on the polymerization/depolymerization of microtubules (MTs) in the cell structure, during spreading and proliferation stages in a cell cycle.

The direct interaction between the SiNWs and the cell membrane can enhance the accuracy and the state of the resultant electrical response of biological cells. The nanowires act as both an adhesive layer (for cell attachment) and a conductive layer (to extract electrical signal from the cells). Accordingly, there is no need for an excess layer of an adhesive material, which is required in the case of titanium-gold (Ti—Au)-nanowires coated ESIC. In addition, the great biocompatibility of SiNW-ECIS produced as disclosed in the present application, makes it a suitable electrical biosensor with the capability of sensing the slim variations in dielectric constants of seeded cells during their membrane extension in the spreading state.

On the other hand, the spreading stage as one of the important pre-proliferation steps or stages (occurring about 10 hours before proliferation stage) would contain many distinguishable parameters between normal and malignant cells. However, as noted above, the impedimetric monitoring of the spreading stage in normal and cancerous cells has not been carried out for diagnosis applications to date. Hence, fabrication of cancer cells ECIS biosensors with the ability to diagnose the cancer cells at their spreading stage could lead to much faster responses and be a helpful alternative for common electrical impedance sensors.

In one implementation, the presented SiNW-ECIS biosensor has a three-layered structure, including: a substrate, a thin catalyst layer formed on the substrate; and a plurality of nanowire electrodes array coated on the catalyst layer. The substrate may be a silicon chip or wafer coated by a layer of silicone dioxide ($SiO_2$). The substrate may have a thickness of about 1 cm or less. The catalyst layer may be made of gold or a bilayer of Ni—Au with a thickness of about 10 nm or less. The plurality of nanowires may include SiNWs grown on a specific patterned zone of the catalyst layer. The SiNWs may have a thickness or diameter in a range of 50 nm to about 90 nm or less.

Figure 1B:
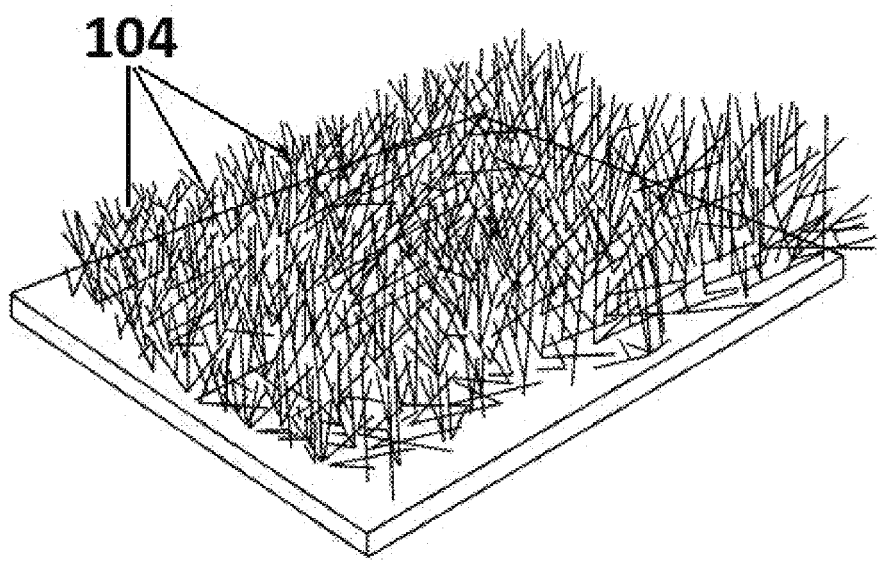
FIG. 1B illustrates a schematic of a plurality of silicon nanowires grown on the sensor region pursuant to the teachings of the present application.

FIG. 1A illustrates a schematic structure of a SiNW-ECIS device 100. The SiNW-ECIS device 100 includes a silicon chip or a silicon wafer 101; a $SiO_2$ layer 102 grown on the silicon chip or silicon wafer 101; and a catalyst layer 103 deposited on the silicon oxide layer 102 and partially patterned in an arbitrary designed region (designated hereinafter as "sensor region"). The sensor region may be considered for growth of nanowires electrode. As shown, the SiNW-ECIS device 100 also includes a plurality of nanowire arrays 104 grown on the patterned catalyst layer 103 in the sensor region. FIG. 1B illustrates the grown SiNWs 104 on the patterned catalyst layer 103.

The SiNW-ECIS device 100 can be fabricated via a method including steps of: first, growing a layer of silicon dioxide ($SiO_2$) 102 on a silicon chip or wafer 101 as a substrate layer; second, coating or depositing a catalyst layer 103 on the grown silicon oxide layer 102; third, patterning and etching the catalyst layer 103 in a region considered as the sensor region transferred on the substrate 101; fourth, growing a plurality of SiNW arrays 104 on the sensor region; and fifth, transferring the prepared SiNW-ECIS device 100 into a doping furnace.

Figure 2:
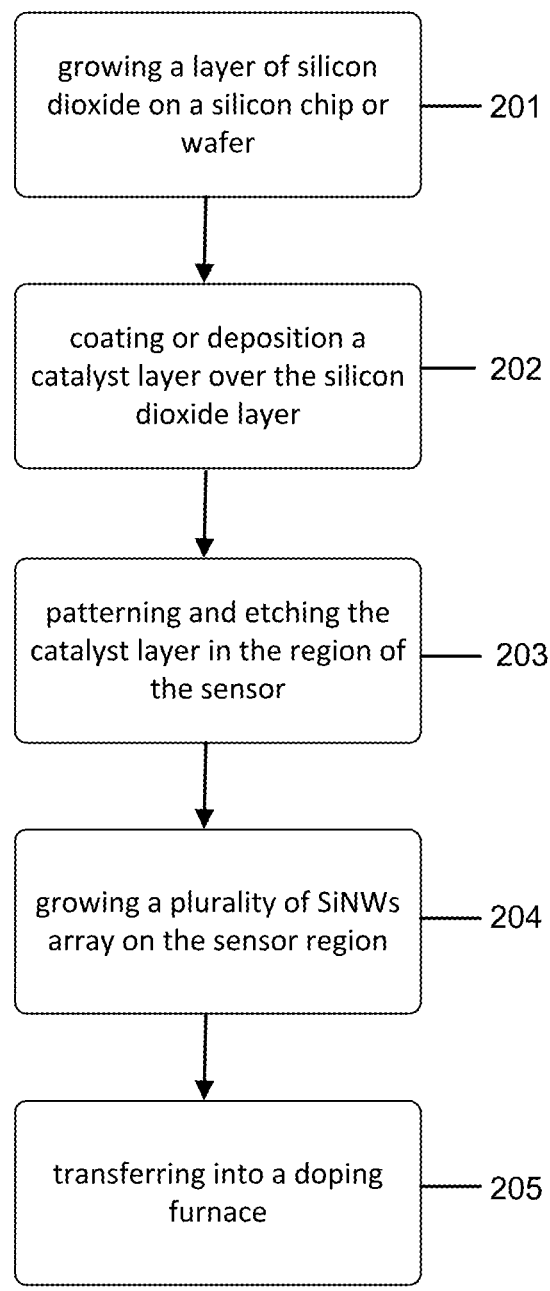
FIG. 2 illustrates an exemplary fabrication method for a SiNW-ECIS device, pursuant to the teachings of the present application.

FIG. 2 shows an exemplary process for fabricating the SiNW-ECIS device 100. Referring also to FIG. 1A, in the first step 201, a layer of silicon dioxide is grown on an initially supplied silicon chip or wafer 101, for example via a wet oxidation furnace or chamber at a temperature of about 1050° C. The silicon oxide 102 may have a thickness of about 250 nm on the silicon chip or wafer 101 having a thickness of about 1 cm or less.

The second step 202 involves coating or depositing a catalyst layer 103 over the silicon oxide layer 102, using, for example, a sputtering system. The catalyst material can be for example gold or a bilayer of Ni—Au, which is deposited or coated with a thickness of about 10 nm.

The third step 203 involves patterning and etching the catalyst layer 103, which may be carried out through a photolithography process. Accordingly, the catalyst layer 103 partially is patterned in a considered region for growing sensor electrodes which is named as the sensor region.

The fourth step 204 involves growing a plurality of SiNWs 104, as the sensor electrodes array on the patterned sensor region over the catalyst layer 103. The SiNWs 104 may be grown via a vapor-solid-liquid (VLS) process using a low-pressure chemical vapor deposition (LPCVD) system. The VLS process may be carried out by the assistance of $H_2$ and $SiH_4$ gases at a temperature of about 450° C.

The fifth or final step 205 involves transferring the as-prepared SiNW-ECIS device 100 into a doping furnace to enhance the conductivity of SiNWs 104. The doping step can be carried out by an element of group five of the periodic table, for example, using a phosphorous doping furnace.

It should be understood that the SiNW-ECISs, designed and fabricated pursuant to the teachings of the present application, may be biocompatible in interaction with a wide range of biological cells. For example, the SiNW-ECISs may be biocompatible with epithelial cells, breast cells, etc.

In another aspect of the present application, a measuring device including the SiNW-ECIS is designed for measuring and recording the electrical response or impedance of a biological cell line.

Figure 3:
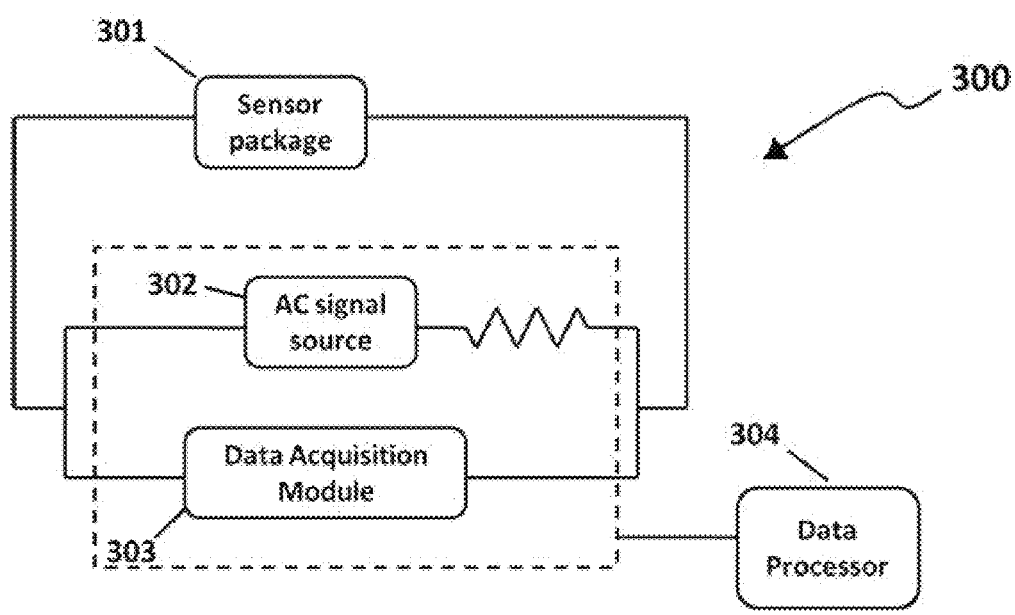
FIG. 3 illustrates a schematic of the device designed for impedance measurements including a sensor package, a system for electrical signal application and data acquisition, and a data processor.

FIG. 3 illustrates a schematic of the measuring device 300 designed for electrical impedance measurements of cells. The device 300 includes a sensor package 301, a system for electrical signal application by an AC signal source 302, a data acquisition module 303, and a data processor 304.

The sensor package 301 includes a SiNW-ECIS device (e.g., the SiNW-ECIS device 100) designed and fabricated pursuant to the teachings of the present application, which can be packed, for example in a glass cover and can be sealed with, for example a biograde silicon rubber tube. The glass may be Plexiglas. The AC signal source 302 and the data acquisition module 303 can be fabricated based on an IC: AD 5933 in an individual board. The AC signal source 302 may be configured to apply different voltages at different frequencies on the sensor package 301. The data acquisition module 303 may be configured to acquire the corresponding resultant electrical responses. The applied voltage can be, for example about 400 mV and the applied frequencies can be, for example, in the range of about 100 Hz to 150 KHz. The data processor 304 may receive the data from data acquisition module 303, record, and draw corresponding curves for further data analysis.

In another aspect of the present application, a method is described for detecting and monitoring the spreading stage of a biological cell via measuring electrical cell impedance using a SiNW-ECIS device. This method may be used for cancer diagnosis, cancerous tumors growth monitoring at metastatic stage, or generally for cancerous state determination of malignant tissues or cells at early stages of cancer progression.

In one implementation, the method for detecting and monitoring the spreading stage of a biological cell includes four main steps of: first, removing and isolating a biological cell line, second, culturing and preparing the cell lines in an appropriate controlled set of conditions, third, seeding the prepared cell lines on the electrode arrays of an ECIS; and fourth, measuring and recording the electrical impedance of the ECIS covered by the cell lines at specific frequencies.

Figure 4:
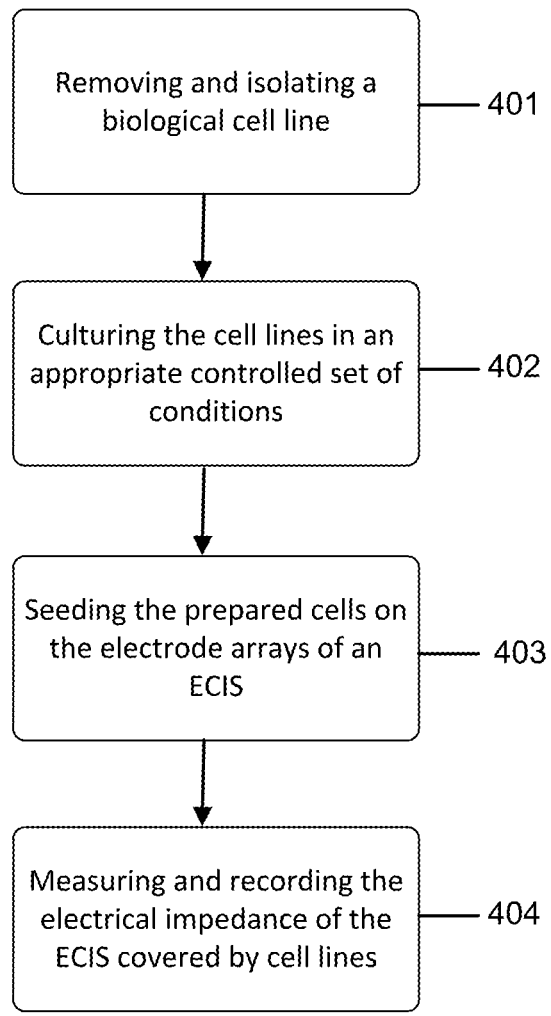
FIG. 4 illustrates an exemplary method for detecting and monitoring the spreading stage of a biological cell using the SiNW-ECIS device shown in FIG. 3.

FIG. 4 shows an exemplary method 400 for detecting and monitoring the spreading stage of a biological cell pursuant to the teachings of the present application. In the first step 401, biological cell lines may be removed and isolated from a normal tissue or malignant cancerous tumor. For example, the biological cell lines may be removed and isolated from the epithelial healthy tissues or tumors. More specifically, the biological cell lines may be, for example, MRC-5 (Medical Research Council 5) cell lines isolated from normal healthy lung tissues or QU-DB cell lines isolated from malignant cancerous lung tissues.

In the second step 402, the isolated cell lines are cultured in an appropriate controlled set of conditions. The isolated cell lines may be maintained in an appropriate medium, such as a Roswell Park Memorial Institute-1640 (RPMI-1640) medium. The medium may be replaced with a fresh medium every day before electrical impedance measurements. Also, the cell lines may be maintained in a $CO_2$ incubator containing $CO_2$ and clean air. The gas composition of incubator may be about 5% for $CO_2$ and 95% for clean air.

In the third step 403, the isolated and cultured cell lines are seeded on the ECIS surface. In one implementation, the ECIS can be a SiNW-ECIS. The third step 403 can include dropping the prepared cell lines on the surface of a packed and sealed ECIS and maintaining the cell lines seeded on the ECIS in an incubator to achieve cell attachment on the SiNWs.

In one implementation, the isolated and cultured cell lines are dropped on the surface of the ECIS with a volume of, for example about 300 µl. Then, the ECIS is maintained in an incubator for complete attachment of the cells to the nanowires. The ECIS can, for example, be maintained in the incubator for about 3 hours to 10 hours. The obtained SiNW-ECISs including the attached cells from the present step are named as "samples" considered for more investigations in the following steps.

The final step 404, involves measuring and recording the electrical impedance of the samples, which is carried out using the measuring device 300 of FIG. 3. The measurement of electrical impedance of the prepared samples can include applying a specific voltage on the ECIS package including the isolated and cultured cells attached to the SiNW electrode arrays; and measuring and reading out the impedance of the samples at various specific frequencies. The impedance measurements can be carried out at frequencies in a range of, for example, about 100 Hz to about 150 KHz.

In another general aspect, a method for measuring and monitoring of the therapeutic effect of anticancer drugs, particularly, antitubulin drugs is proposed in the present application. The method is based on the effect of the polymerization/depolymerization process rate of microtubules (MTs) on the bioelectrical properties of a cell membrane, particularly, the electrical impedance of biological cells. Additionally, the method reliability can be investigated by standard tests, such as Confocal, flowcytometry and tubulin assembly assays. The results from foregoing tests may be used to observe the mechanism in which antitubulin drugs cause electrical response variations of the cancerous cells due to their therapeutic effects through polymerization/depolymerization process rate variations of MTs in cell cytoskeleton.

It should be understood that MTs, as one of the key components in cytoskeleton with crucial role in metabolisms and disease transformation of mammalian cells, interact extensively and intimately with cellular membranes. The MTs make up the internal structure of cilia and flagella, which are covered by an extension of the plasma membrane. In addition, tubulin and membrane proteins are bound with each other by Ankyrins, including the cell-cell adhesion proteins, E-cadherin and the $Na^+/K^+$ ATPase in epithelial cells. Ankyrin-G also binds $Na^+$ channel and $\beta$-subunits. MTs are also involved in exocytosis and endocytosis initiated by the membrane. Hence, any disruption in MTs structure and function, such as polymerization or depolymerization rate variations caused by antitubulin drugs can induce dramatic changes in the shape and function of the membrane. Therefore, these changes might rapidly affect the electrical responses of the membrane, because biological functions of the membrane affect their electrical activities. Accordingly, when the function and dielectric properties of the membrane is affected by MTs disruption, the current penetration into the membrane would be changed significantly.

Accordingly, a method is described in the present application for detection and monitoring the therapeutic effects of specific cancer treatment drugs via measuring electrical cell impedance of the membrane of target cells, using a device based on SiNW-ECIS. This method can be used for investigating and detecting the therapeutic effect of, for example, antitubulin drugs in cancer treatments. Also, the method may be used for determining the dosage of antitubulin drugs in cancer treatments.

Figure 5:
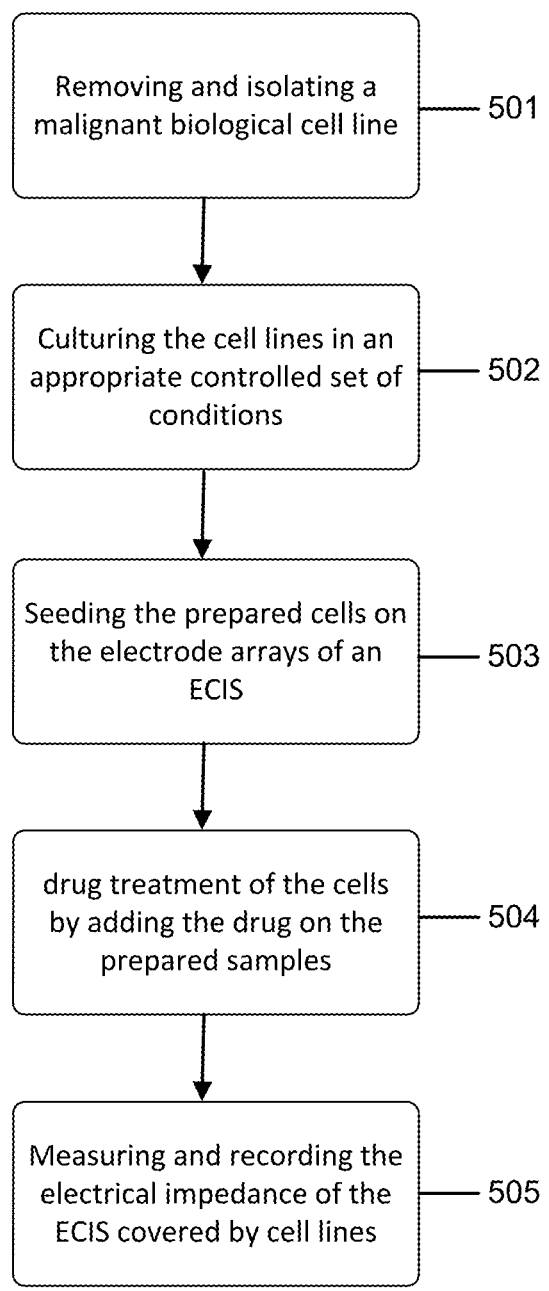
FIG. 5 illustrates an exemplary process for detecting and monitoring the therapeutic effect of specific cancer treatment drugs using the SiNW-ECIS device shown in FIG. 3.

FIG. 5 illustrates an exemplary method 500 for detection and monitoring the therapeutic effects of specific drugs using the measurement device 300 shown in FIG. 3. The method 500 includes five main steps of: removing and isolating a malignant biological cell lines (step 501); culturing and preparing the cell lines in an appropriate controlled set of conditions (step 502); seeding the prepared cell lines on the electrode arrays of an ECIS device (e.g., the SiNW-ECIS device 100) (step 503); treating the cell lines by adding a drug on the seeded cell lines (step 504); and finally, measuring and recording the electrical impedance of the ECIS device, which is covered by treated cell lines, at specific frequencies (step 505).

In the first step 501, the biological cell lines may be removed and isolated from a malignant cancerous tumor. For example, the biological cell lines may be removed and isolated from a breast tumor. The biological cell lines may be the MCF-7 (Michigan Cancer Foundation-7) cell lines isolated from a breast tumor.

In the second step 502, the isolated biological cell lines are cultured in an appropriate controlled set of conditions. Accordingly, the isolated cell lines are maintained in an appropriate medium, such as a Roswell Park Memorial Institute-1640 (RPMI-1640) medium. The medium may be replaced with a fresh medium every day before electrical impedance measurements. The isolated cell lines can be maintained in a $CO_2$ incubator containing 5% $CO_2$ and 95% clean air, at a temperature of about 37° C.

In the third step 503, the cultured cell lines are seeded on the ECIS surface. The ECIS may be the SiNW-ECIS device 100 shown in FIG. 1. The third step 503 involves dropping the cultured cell lines on the surface of the packed and sealed ECIS device and maintaining the packed and sealed ECIS device containing the dropped cell lines in an incubator to achieve cell attachment on the SiNWs. The cultured cell lines may be dropped on the surface of the packed and sealed ECIS device with a volume of, for example about 300 µl. Then, the packed and sealed ECIS device can be maintained in an incubator for complete attachment of the cell lines to the nanowires. In one specific example, the packed and sealed ECIS device can be maintained in an incubator for about 3 hours to about 10 hours. The obtained ECIS device including the attached cell lines may be considered "samples" and used for more investigations in the following steps.

In the fourth step 504, anti-cancer drugs with specific amounts are added to the samples after cell attachment on the SiNWs for treatment of the cells. Then, the samples are maintained in an incubator for a desired time interval. The anti-cancer drugs can be, for example antitubulin drugs such as Albendazole (ABZ), Paclitaxel (PTX) or any other antitubulin drug. The drug may have a concentration of, for example about 0.1 to 20 nano-mole per liter. The treated samples can be maintained in an incubator for at least about 2 hours before electrical assay.

In the final step 505 the electrical impedance of the treated cells is measured and recorded using the measuring device 300 shown in FIG. 3. The measurement of the electrical impedance of the treated cells includes applying a specific voltage on the ECIS package including the treated cells attached to the SiNW electrode arrays and measuring and reading the impedance of the samples at various specific frequencies. The impedance measurements can be carried out at frequencies in a range of, for example, about 100 Hz to about 150 KHz.

Exemplary techniques for the fabrication of SiNW-ECIS and their use for monitoring the spreading stage of biological cells or therapeutic effect of anti-cancer drugs, pursuant to the teachings of the present application are set forth hereinbelow. It should be understood that these examples are illustrative only, and similar techniques for fabrication of SiNW-ECIS and their use according to the instant application are thus possible with different parameters, as is all well understood to those of skill in the art. The examples should not be deemed as limiting the scope of the present application. The only limitations of the scope of the instant case are set forth in the claims appended hereinbelow.

Example 1: Fabrication of SiNW-ECIS

In this example, a silicon wafer having a thickness of about 0.5 cm is used as the substrate. First, the silicon wafer was cleaned through the standard RCA#1 cleaning method ($NH_4OH$: $H_2O_2$: $H_2O$ solution and volume ratio of 1:1:5). Subsequently, a thin layer of $SiO_2$ with a thickness of about 300 nm was grown on the substrate by a wet oxidation furnace at a temperature of about 1050° C. Then, a 10 nm thin gold layer was coated on the $SiO_2$ layer, as the catalyst layer by a sputtering system (Veeco Co.). Then, the gold layer was patterned to form a sensor region on the substrate. Then, the substrate with the patterned gold layer was placed in a LPCVD system (SensIran Co. Iran) and SiNWs were grown in the sensor region by the assistance of $H_2$ and $SiH_4$ gases at a pressure of about 1 mTorr and a temperature of about 450° C. to form the SiNW-ECIS. Finally, the SiNW-ECIS was transferred into a phosphorous doping furnace to enhance the conductivity of the nanowires by the diffusion of phosphorous dopants atoms.

Figure 6A:
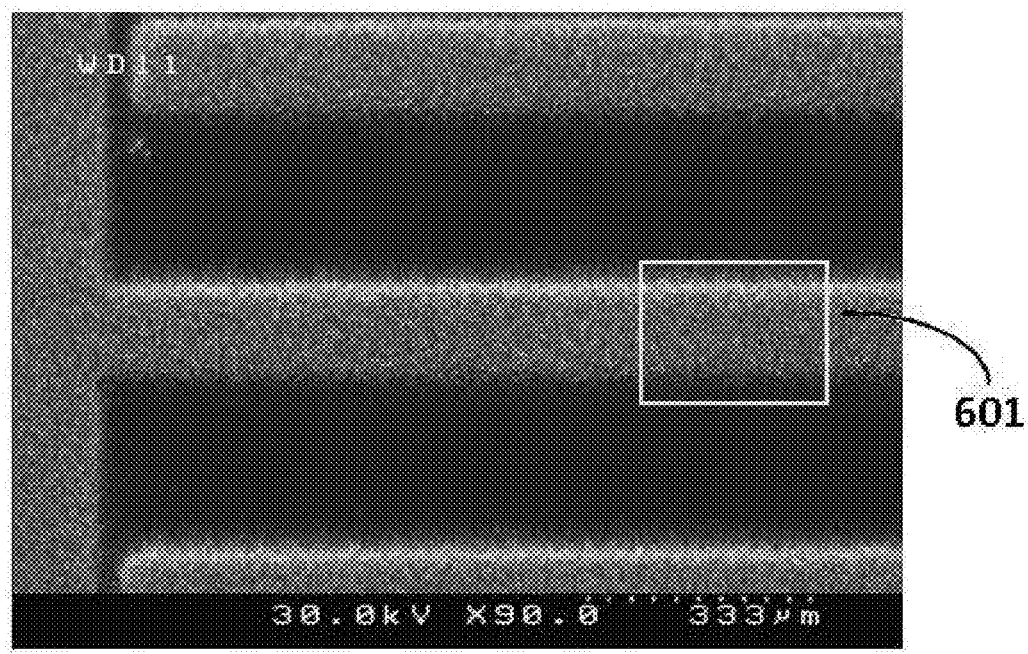
FIG. 6A illustrates an exemplary scanning electron microscope (SEM) image of SiNW-ECIS prepared pursuant to the teachings of the present disclosure, showing the geometry and architecture of SiNW-ECIS with a reference scale of 333 μm.
Figure 6B:
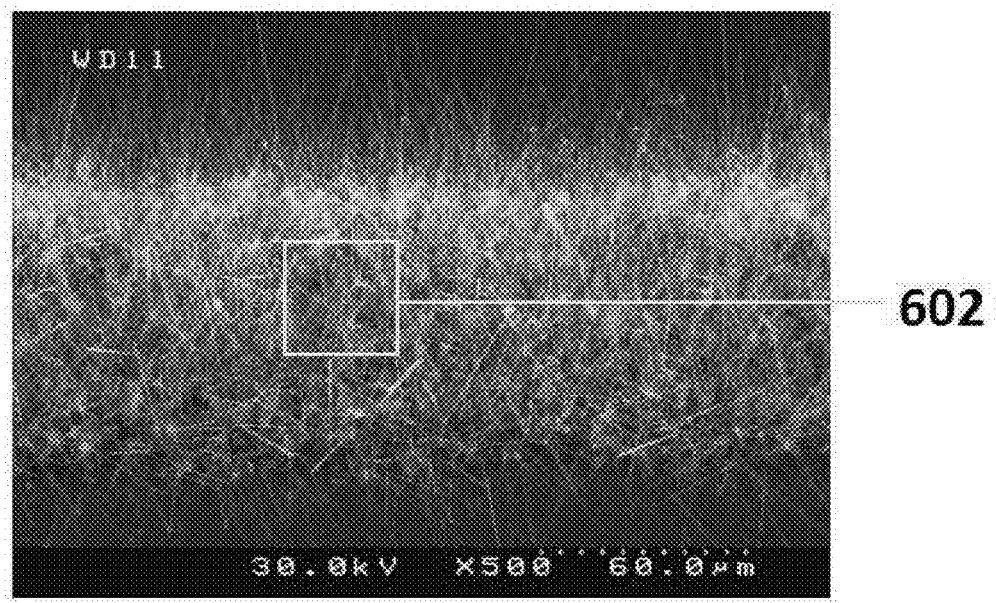
FIG. 6B illustrates an exemplary SEM image of SiNW-ECIS prepared pursuant to the teachings of the present disclosure, showing the geometry and architecture of SiNW-ECIS with a reference scale of 60.0 μm.
Figure 6C:
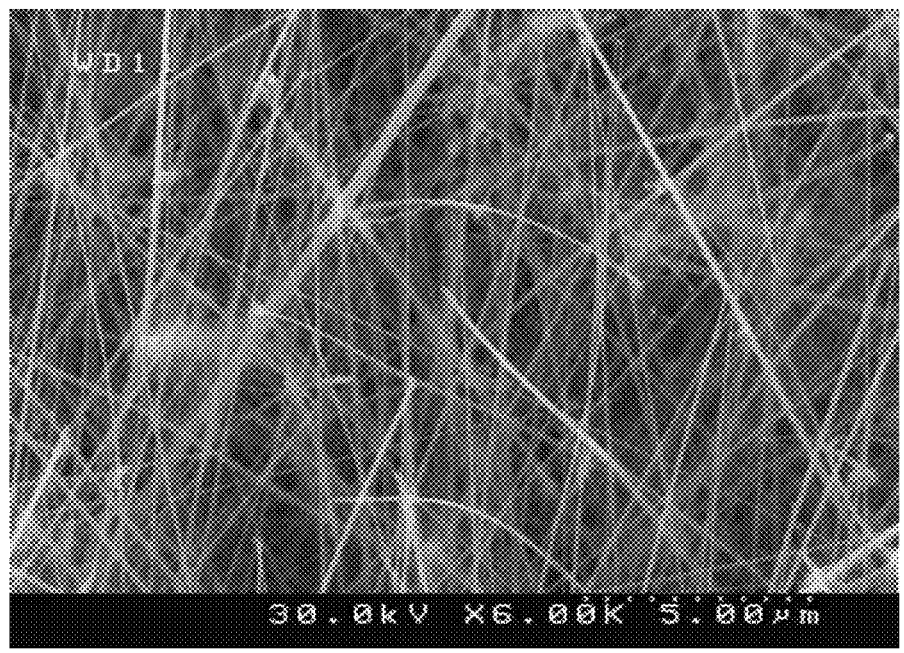
FIG. 6C illustrates an exemplary SEM image of SiNW-ECIS prepared pursuant to the teachings of the present disclosure, showing the geometry and architecture of SiNW-ECIS with a reference scale of 5.00 μm.

FIG. 6A illustrates a SEM image of the SiNWs array grown in the patterned sensor region. For a better observation, a greater magnification of the grown SiNWs of as-prepared SiNW-ECIS of the part 601 is shown in FIG. 6B. In addition, an even more magnified SEM image of the part 602 representing the grown SiNWs and their geometry and architecture are shown and FIG. 6C. It can be seen that SiNWs were grown with a uniform size and structure in nanometer scales and are well distributed over the patterned sensor region.

Example 2: Investigation of Biocompatibility of SiNWs

To investigate the biocompatibility of the silicon nanowires, an MTT (3-(4,5-Dimethylthiazol-2-yl)-2,5-Diphenyltetrazolium Bromide) assay was applied in this exemplary implementation of the present application. In the MTT assay, the viability of the cells is verified based on a colorimetric measurement as is known in the art. Initially, the surface of the device was sterilized using an autoclave before cell seeding process. Then, the QU-DB cell lines were seeded and attached on SiNW surface according to the method described hereinabove.

Figure 7:
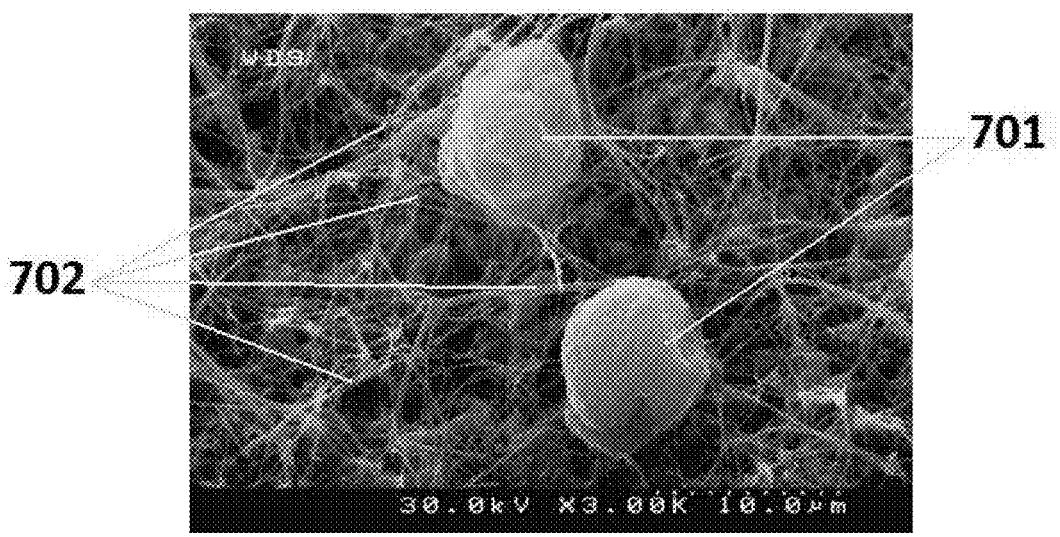
FIG. 7 illustrates an exemplary SEM image of SiNW-ECIS prepared pursuant to the teachings of the present application, showing the geometry and architecture of SiNWs after the cells interactions and attachment with the silicon nanowires.

FIG. 7 illustrates an SEM image of the silicon nanowires after cells interaction with silicon nanowires on the sensor region. The attachment of cells 701 onto the SiNWS 702 with no need to an adhesive can be observed from this figure in comparison with referring again to FIG. 6C, which shows the SiNWs before any interaction with cell lines.

After 24 hours, the QU-DB cell lines were removed from the substrate by trypsin and the culture media was added to the cell solution. Subsequently, the cells were placed in the wells of a sterile 96 well micro plate with the same concentration and the MTT protocol was applied on each well. In this regard, 10 μl of MTT solution with the concentration of 5 mg/μl was added to each well. The wells were incubated for 4 hours in a 5% $CO_2$ ambient at 37° C. Next, the float materials were removed from the surface of the wells and 100 μl of dimethyl sulfoxide was added to each well. After 20 min stirring of each well (in order to dissolving the formazane), the optical absorption of each well containing the cell lines was calculated in 493 nm by micro plate reader system so that the percentage of viable cells versus the control well can be calculated.

Figure 8A:
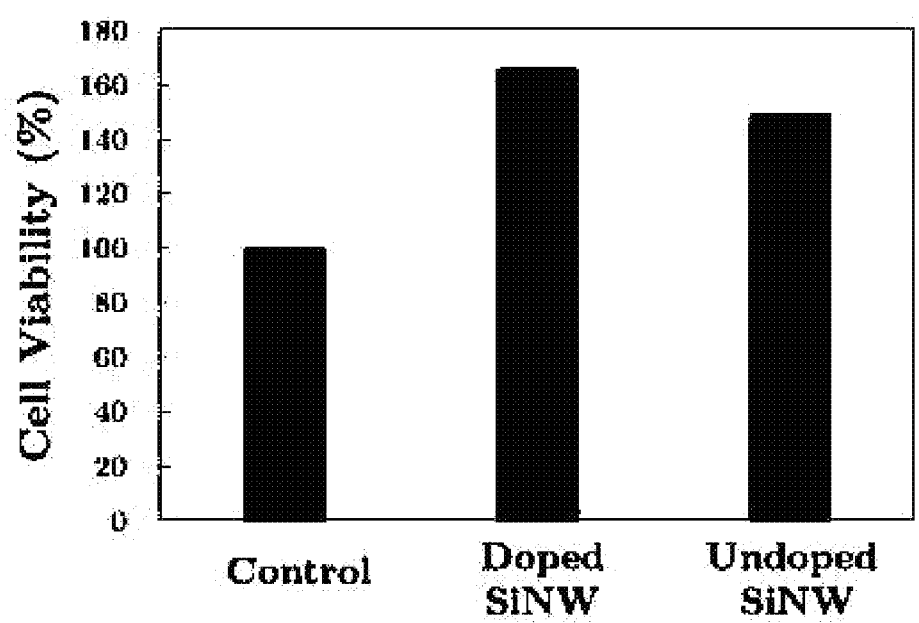
FIG. 8A illustrates MTT (3-(4,5-Dimethylthiazol-2-yl)-2,5-Diphenyltetrazolium Bromide) assay results of a sample of lung tumor cells (QU-DB cell lines) seeded on SiNW-ECIS with doped and un-doped silicon nanowires.

FIG. 8A illustrates MTT assay results of QU-DB cells seeded on SiNW-ECIS with doped and undoped silicon nanowires. This figure shows a 60% viability increase for the seeded cells on doped SiNWs and a 40% viability increase using undoped SiNWs after 24 hours, in comparison with a control sample. The results indicate that such nanostructured surface, improved the growth and proliferation of cells in respect to well plate surface.

Furthermore, the biocompatibility of SiNWs was investigated taking the florescent images from the QU-DB cells covered on individual devices before and after proliferation stages of the seeded cells (taken 6 hours and 12 hours after the cells culturing on the surface).

Figure 8B:
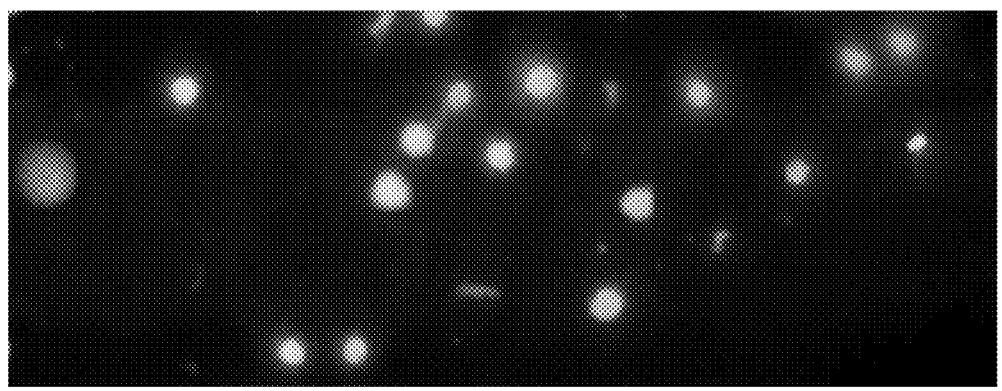
FIG. 8B illustrates Florescent images of QU-DB cells seeded on SiNW-ECIS before proliferation stage.
Figure 8C:
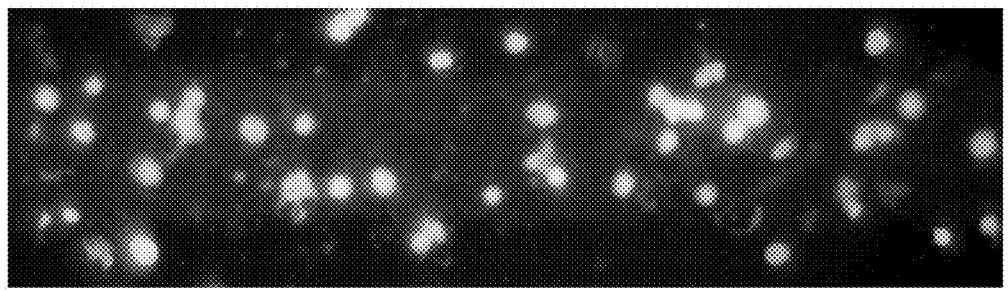
FIG. 8C illustrates Florescent images of QU-DB cells seeded on SiNW-ECIS after proliferation stage.

The florescent images of cells are illustrated before the proliferation stages as shown in FIG. 8B and after the proliferation stages as shown in FIG. 8C. In these images, the white dots are cells which are colored for the florescent test. It can be observed that the number of cells was significantly increased after 12 hours, which shows that the cells growth cycle is continued after attachment of cells onto the SiNWs. Accordingly, these images corroborate the vitality of the cells as well as their stable biological metabolism after attachment on SiNWs.

Example 3: Monitoring the Spreading Stage of Biological Cells Using SiNW-ECIS

In this example, initially MRC-5 was isolated form normal human lung tissue and QU-DB cell lines were isolated from malignant human lung tissue. These cells were obtained from the standard cell Banks of Iran (Pasteur Institute). The cells were cultured by maintaining in a $CO_2$ incubator at 37° C. (5% $CO_2$, 95% clean air) in a RPMI-1640 medium (Sigma 8758) supplemented with 5% fetal-bovine serum (Gibco), and 1% penicillin/streptomycin (Gibco). The fresh medium was replaced every day. Then, the same concentrations of MRC-5 and QU-DB cells (104#/ml) were dropped on the surface of the SiNW-ECIS device with final volume of 300 μl. In one implementation, the SiNW-ECIS device is packed in a plexiglass cover sealed with biograde silicon rubber tube. Then, the SiNW-ECIS device was held in an incubator (new brunswik Co.) and the electrical measurements were carried out after the desired period of times.

Figure 9A:
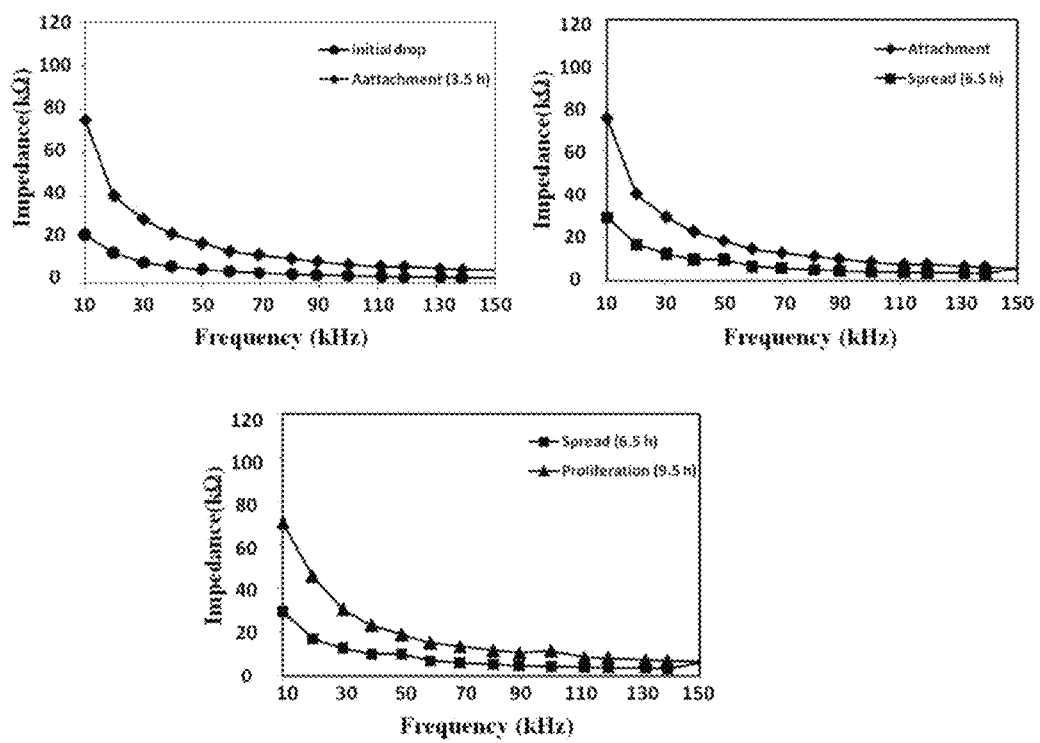
FIG. 9A illustrates comparative impedance values recorded by the SiNW-ECIS device covered by QU-DB cell lines during different culturing stages: initial drop-attachment (top left); attachment-spreading (top right); spreading-proliferation (bottom)
Figure 9B:
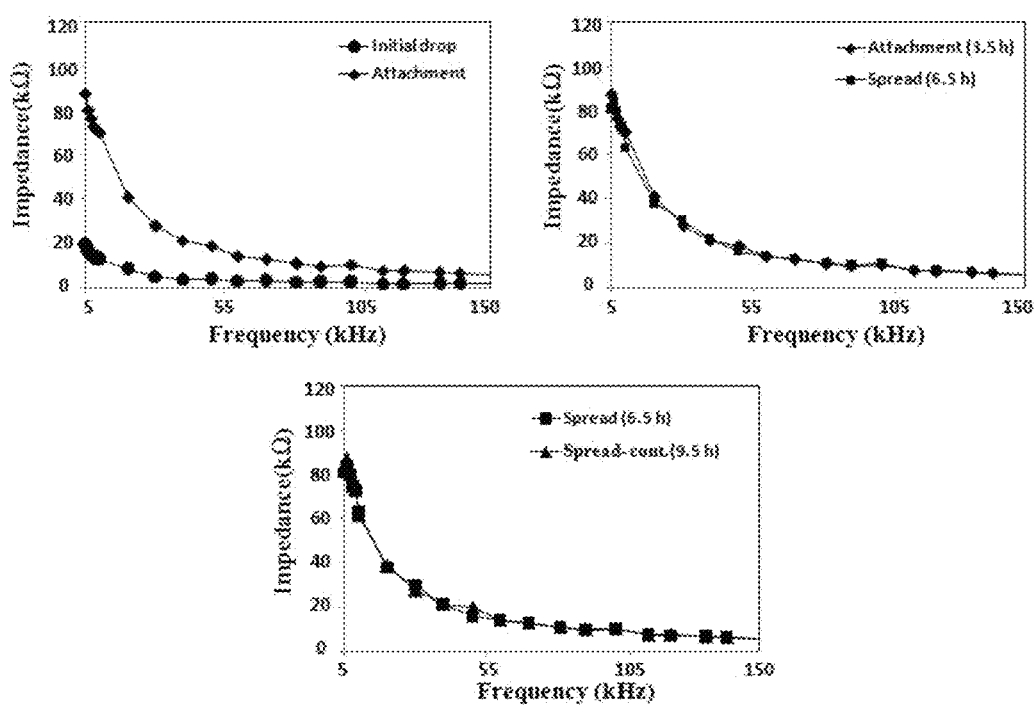
FIG. 9B illustrates comparative impedance values recorded by the SiNW-ECIS device covered by MRC-5 cell lines during different culturing stages: initial drop-attachment (top left), attachment-spreading (top right); and spreading (bottom)

FIGS. 9A and 9B illustrate comparative impedance values measured for SiNW-ECIS covered by QU-DB and MRC-5 cells during different culturing stages, including 0-3.5 hours (Top-left), 3.5-6.5 hours (Top-right) and 6.5-9.5 hours (Bottom) after the initial drop. It can be observed from these figures that the impedance has been increased during the first interval of culturing time (3.5 hours from initial drop) representing the cells attachment stage for both QU-DB (FIG. 9A, Top-left) and MRC-5 cells (FIG. 9B, Top-left). Accordingly, no observable difference between the electrical pattern of cancerous and healthy cells is observed during the attachment stage. This impedance increment is due to a well demand with dielectric properties of the cells resulted in current blocking and impedance increase after direct attachment of the cells on nanowires.

Referring again to FIG. 9A, the top-right sided chart illustrates the spreading stage of QU-DB cells during 3 hours after the attachment of the malignant cells, where the impedance of the sensor is reduced in comparison with the attachment stage. In contrast, the proliferation stage (about 3 hours after spreading) of QU-DB cells had increasing effect on the impedimetric response of SiNW-ECIS as illustrated in the bottom sided chart.

Referring again to FIG. 9B, no noticeable impedance variation was measured for normal cells (MRC-5) during the second and third time intervals (about 6 hours after the attachment phase), indicating that the aforesaid two stages do not affect the response of SiNW-ECIS covered by normal or healthy cells. This is due to the fact that once the QU-DB cells enter the proliferation stages, normal cells (designated by 'MRC-5') still stayed in spreading stage because of their so slower proliferation rates. Thus, the impedance measurements carried out via SiNW-ECIS device covered by normal and malignant cells would be an appropriate criterion for cancer diagnosis or cancerous state detection.

FIGS. 10A to 10G illustrate the field emission scanning electron microscope (FESEM) images of seeded cancer (QU-DB) and healthy normal (MRC-5) cells at different stages. It is shown in these figures that normal cells have slower proliferation rate and require further time for spreading and membrane extension in respect to malignant ones as described hereinbelow.

Figure 10A:
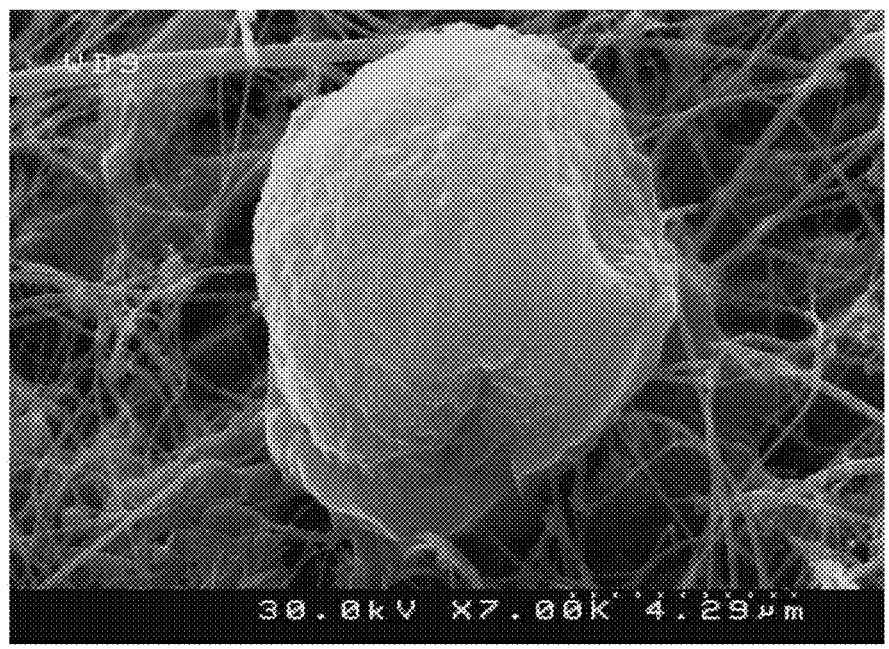
FIG. 10A illustrates a field emission electron microscope (FESEM) image of a single QU-DB cell seeded on SiNW-ECIS at an initial drop stage.

FIG. 10A illustrates a FESEM image of a single QU-DB cell seeded on SiNW-ECIS at the initial drop stage, pursuant to the teachings of the present application.

Figure 10B:
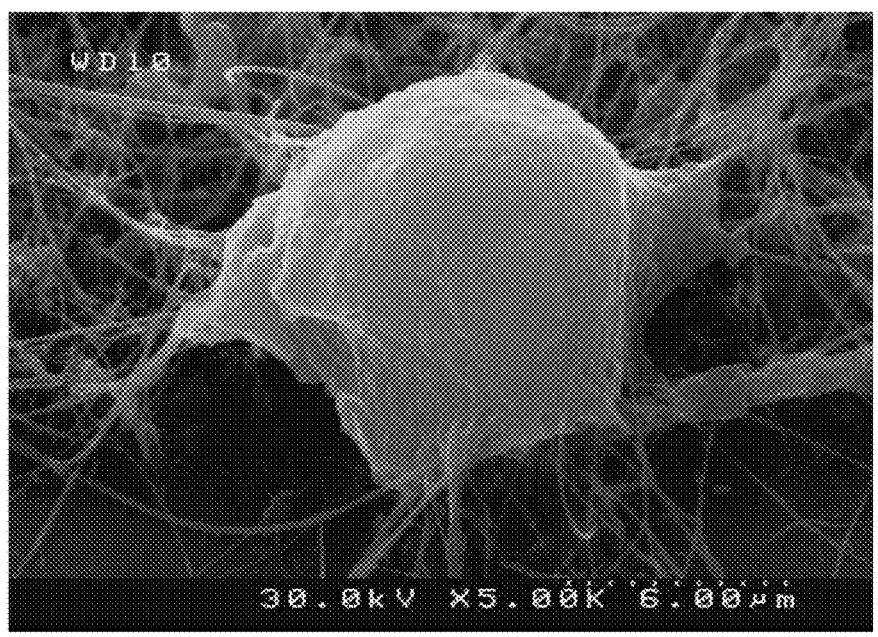
FIG. 10B illustrates a FESEM image of a single QU-DB cell cultured on SiNW-ECIS at an attachment stage.

FIG. 10B illustrates a FESEM image of a single QU-DB cell cultured on SiNW-ECIS at an attachment stage, 3.5 hours after the initial dropping. As shown, after interaction of QU-DB cells with NWs (FIG. 10A), the cells begin to attach onto nano sites of SiNW and their presence result in current flow blocking between inter-digital transducers (IDTs) due to beta dispersion phenomena, as shown in FIG. 9A discussed hereinabove.

Figure 10C:
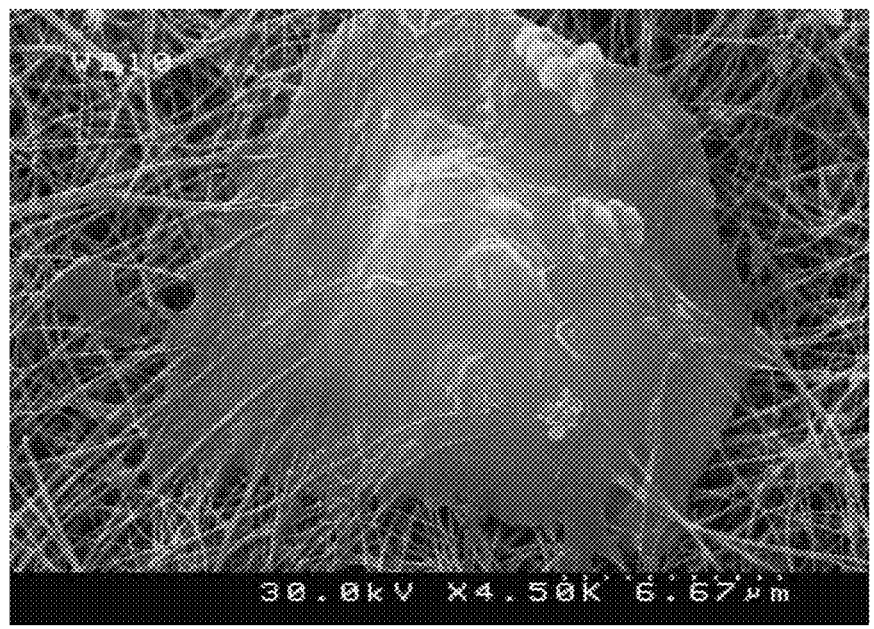
FIG. 10C illustrates a FESEM image of a single QU-DB cell cultured on SiNW-ECIS at a spreading stage.

FIG. 10C illustrates a FESEM image of a single QU-DB cell cultured on SiNW-ECIS at a spreading stage, 6.5 hours after the initial dropping. When the attached cancer cells are entered to spreading sequence, their membrane would be extended. As the membranes of malignant cells are degraded and their dielectric parameters are disrupted during cancerous transformation, stretching of such cells reduced their membrane ability to block the current flow. So, the impedance value of SiNW-ECIS decreased in spreading sequence of malignant cells, as shown in FIG. 9A discussed hereinabove.

Figure 10D:
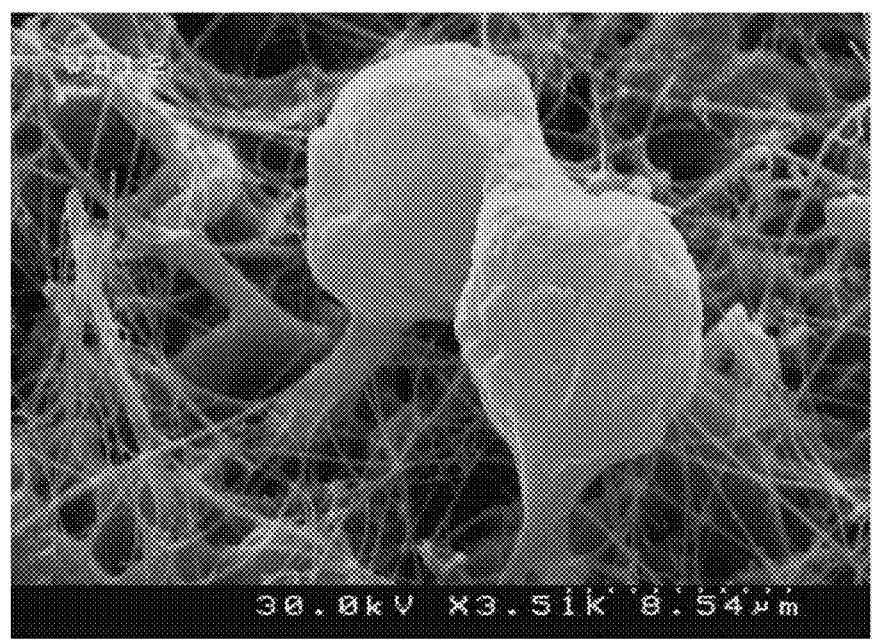
FIG. 10D illustrates a FESEM image of a single QU-DB cell cultured on SiNW-ECIS at a proliferation or a mitosis stage.

FIG. 10D illustrates a FESEM image of a single QU-DB cell cultured on SiNW-ECIS at a proliferation or a mitosis stage, 9.5 hours after the initial dropping. It can be seen that after 9.5 hours, the malignant cells are split and proliferated so that the electrical impedance is increased as shown in FIG. 9A discussed hereinabove.

Figure 10E:
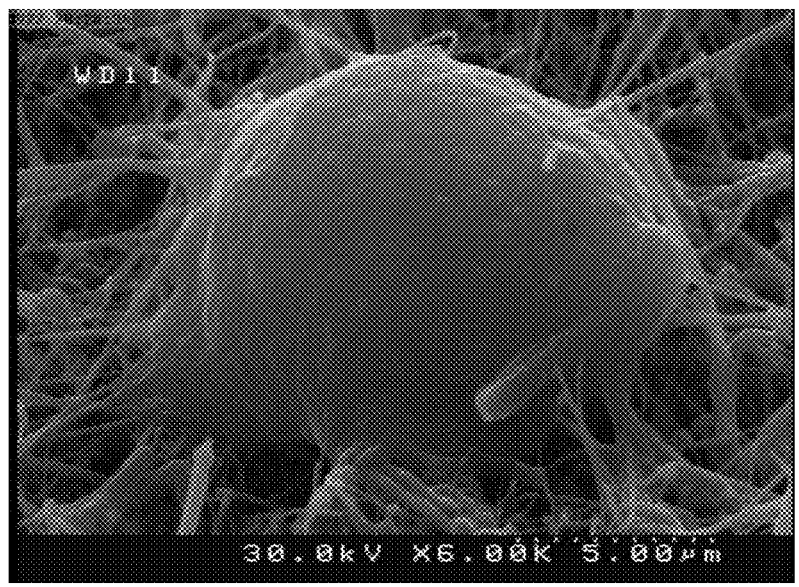
FIG. 10E illustrates a FESEM image of a single MRC-5 cell cultured on SiNW-ECIS at an attachment stage.
Figure 10F:
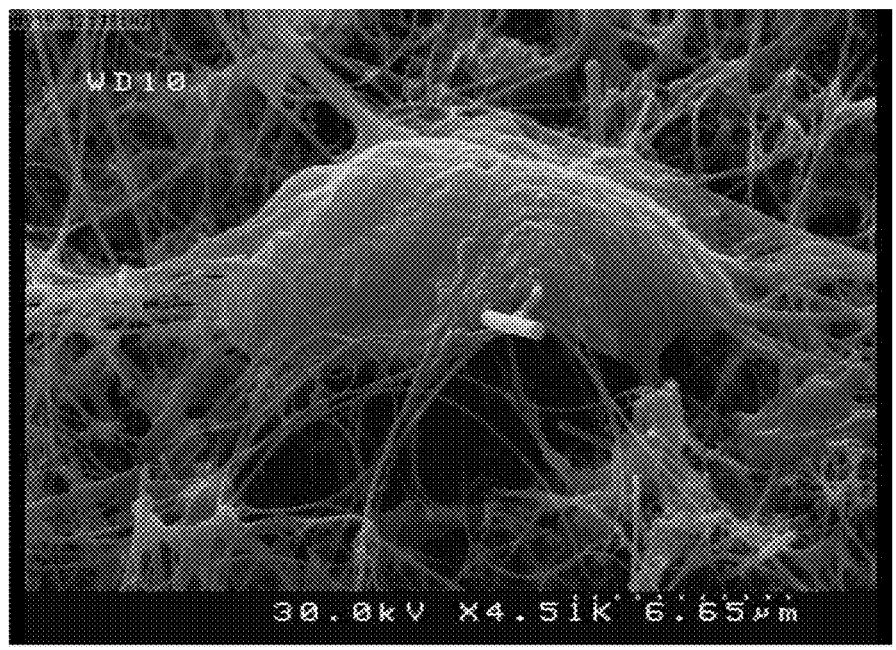
FIG. 10F illustrates a FESEM image of a single MRC-5 cell cultured on SiNW-ECIS at a spreading stage.
Figure 10G:
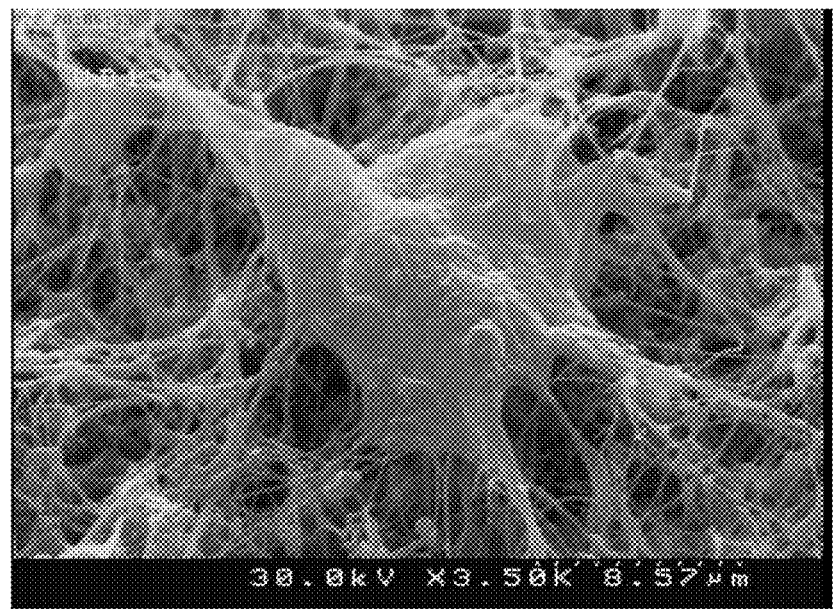
FIG. 10G illustrates a FESEM image of a single MRC-5 cell cultured on SiNW-ECIS at a continued spreading stage.

Referring to FIGS. 10E, 10F and 10G, FESEM images of a single MRC-5 cell cultured on SiNW-ECIS are illustrated at different time intervals from initial dropping. These figures show the cell at attachment, spreading and continued spreading after 3.5 hours, 6.5 hours and 9.5 hours after the initial dropping.

It can be observed that the attachment of the normal cells (FIG. 10E) is led to the current flow blocking similar to cancerous cells, as shown in FIG. 9A discussed hereinabove. In addition, similar extension of the membrane on nanowire occurs during the spreading sequence of normal cells (FIG. 10F), but as their membrane contains non degraded phospholipids and fatty acids their ability in current flow blocking is not disrupted. Therefore, the current cannot penetrate toward their extended membrane and no impedance reduction was measured in SiNW-ECIS covered by MRC-5 cells during spreading sequence (FIG. 9B). On the other hand, the proliferation rate of a normal cell is so slower than malignant one; thus, the MRC-5 cells do not complete the spreading stage after 9.5 hour as seen in FIG. 10G.

Figure 11A:
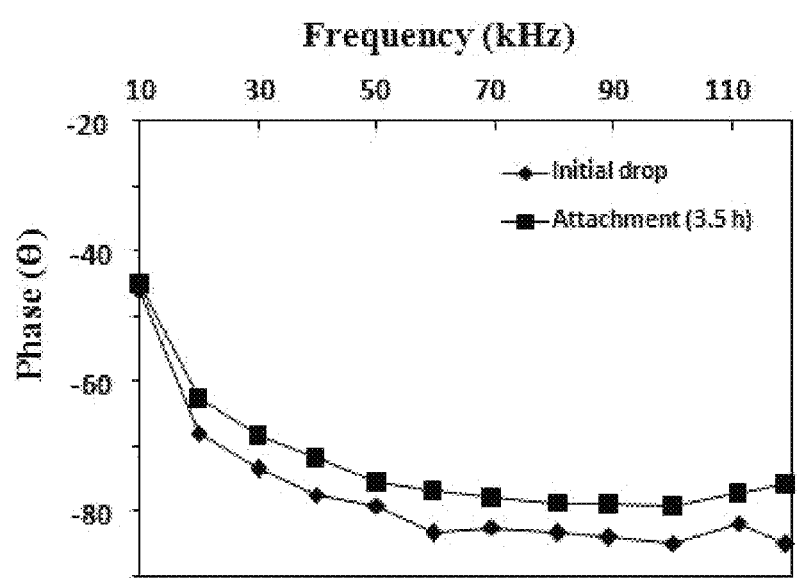
FIG. 11A illustrates the impedance phase diagram of malignant lung cell (QU-DB) cultured on SiNW-ECIS reported from five individual tests at different frequencies for an initial dropping (designated by the symbol ♦) and cells attachment (designated by the symbol ■) after 3.5 hours.
Figure 11B:
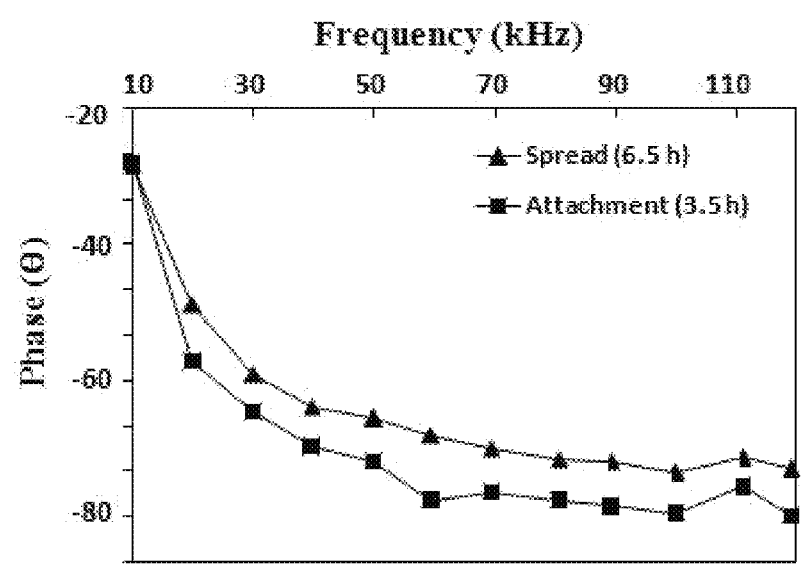
FIG. 11B illustrates the impedance phase diagram of QU-DB cultured on SiNW-ECIS reported from five individual tests at different frequencies for cells attachment (designated by the symbol ■) after 3.5 hours and a spreading stage (designated by the symbol ▲) after 6.5 hours.
Figure 11C:
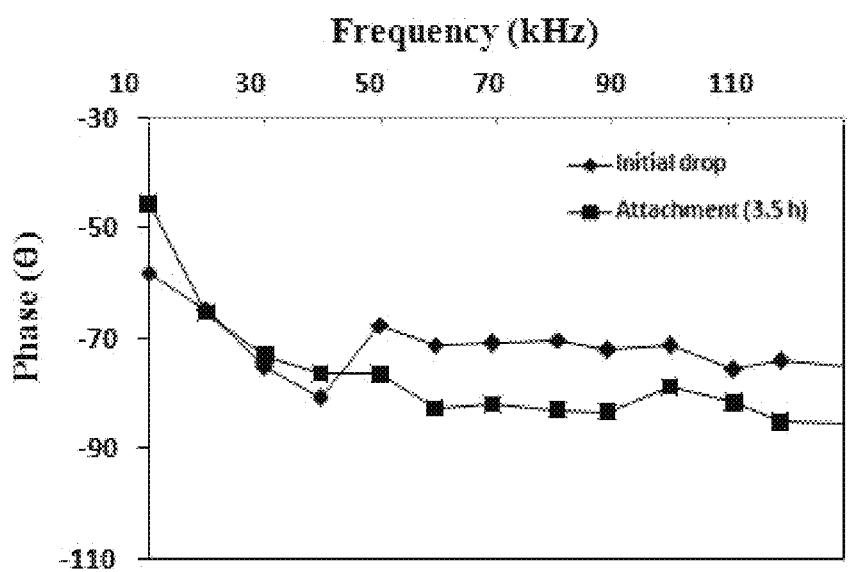
FIG. 11C illustrates the impedance phase diagram of normal lung cell (MRC-5) cultured on SiNW-ECIS reported from five individual tests at different frequencies for an initial dropping (designated by the symbol ♦) and cells attachment (designated by the symbol ■) after 3.5 hours.
Figure 11D:
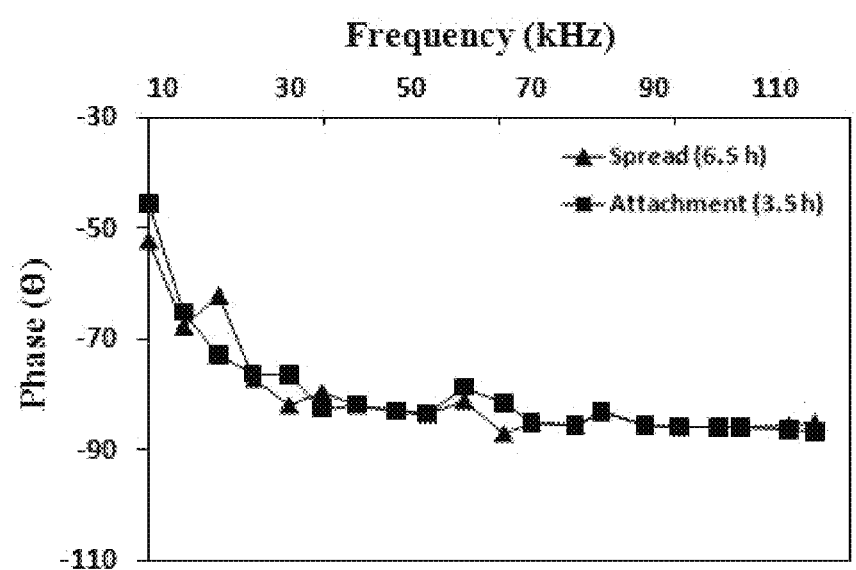
FIG. 11D illustrates the impedance phase diagram of MRC-5 cultured on SiNW-ECIS reported from five individual tests at different frequencies for cells attachment (designated by the symbol ■) after 3.5 hours and a spreading stage (designated by the symbol ▲) after 6.5 hours.

FIGS. 11A-D illustrate the impedance phase diagrams in a complementary confirmation with impedance value diagrams of FIG. 9. FIG. 11A illustrates the impedance phase diagram of malignant lung cell (QU-DB) cultured on SiNW-ECIS reported from five individual tests at different frequencies for initial dropping (designated by the symbol ♦) and cells attachment (designated by the symbol ■) after 3.5 hours. FIG. 11B illustrates the impedance phase diagram of QU-DB cultured on SiNW-ECIS reported from five individual tests at different frequencies for cells attachment (designated by the symbol ■) after 3.5 hours and spreading stage (designated by the symbol ▲) after 6.5 hours. FIG. 11C illustrates the impedance phase diagram of normal lung cell (MRC-5) cultured on SiNW-ECIS reported from five individual tests at different frequencies for initial dropping (designated by the symbol ♦) and cells attachment (designated by the symbol ■) after 3.5 hours. FIG. 11D illustrates the impedance phase diagram of normal lung cell (MRC-5) cultured on SiNW-ECIS reported from five individual tests at different frequencies for cells attachment (designated by the symbol ■) after 3.5 hours and spreading stage (designated by the symbol ▲) after 6.5 hours.

It can be observed that the impedance phase of both QU-DB and MRC-5 cells are increased (in negative values) during the attachment stage which are represented by FIGS. 11A and 11C. Furthermore, the phase of QU-DB cells decreased during spreading stage (shown in FIG. 11B), meanwhile no changes in such stage for normal cells are observed in all of measured frequencies as shown in FIG. 11D.

Example 4: Detection of the Therapeutic Effect of Anti-Cancer Drugs Using SiNW-ECIS In this example, the diagnostic response of cells membrane to extremely low dose of antitubulin drugs is investigated. Initially, MCF-7 cell lines, isolated from grade I human breast tumors, were obtained from the National Cell Bank of Iran (Pasteur Institute). Then, cells were maintained in a $CO_2$ incubator (37° C., 5% $CO_2$) in RPMI-1640 medium supplemented with 5% fetal bovine serum, and 1% penicillin/streptomycin. The fresh medium was replaced every other day. Then, the cultured cells were dropped on the surface of the SiNW-ECIS, designed and fabricated pursuant to teachings of the present application. Prior to each experiment, cells were trypsinized to be detached from the substrate and resuspended on the SiNW surface. To minimize the effect of trypsinization, the procedure may last for less than 4 minutes at room temperature of about 20° C. The samples were held in an incubator for about 4 hours to achieve cells attachment on the SiNWs. Thereafter, the ABZ drug with low concentrations of about 2.1 nano-moles per liter and the PTX drug with low concentrations of about 0.1 nano-moles per liter were added to individual samples. Finally, the signal recording and biological assays were investigated about 2 hours and 6 hours after the drug treatment (6 hours and 10 hours after the beginning of culturing process).

Referring to FIGS. 12A-12G, comparative normalized diagrams of impedance (designated by $\Delta Z$ % and represented by solid black lines) and capacitance changes (designated by $\Delta C$ % and represented by dashed grey lines) are illustrated for MCF-7 cells seeded on SiNW electrodes after treating by 2.1 nano-moles per liter of ABZ and 0.1 nano-moles per liter of PTX. The time interval between the drug incubation and the signal extraction are 2 hours (designated by T1) and 6 hours (designated by T2). In addition, the same diagrams are plotted for control sample prepared with no drug treatment stage.

Figure 12A:
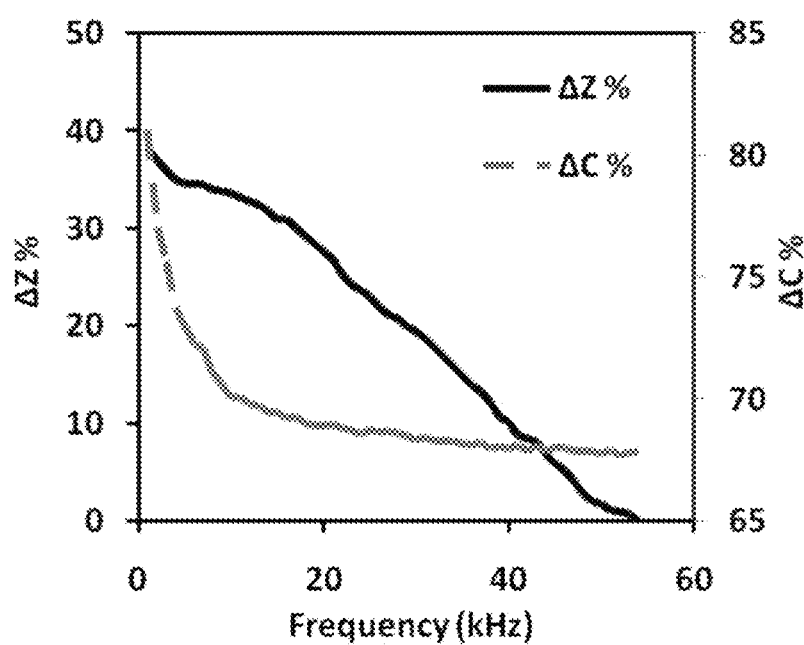
FIG. 12A illustrates the normalized diagram of impedance and capacitance changes for MCF-7 cells seeded on SiNW nano electrodes 2 hours (T1) after treating by 2.1 nanomoles per liter of Albendazole (ABZ) versus the control sample.

Referring to FIG. 12A, the comparative normalized impedance changes between control and ABZ (2.1 nano-moles per liter) treated MCF-7 cells 2 hours after drug incubation (6 hours after dropping the cells on SiNW electrodes) are illustrated. The evaluation of the diagram indicates that ABZ treating induced meanly 25% changes in the membrane impedance of MCF-7 cells after 2 hours. Also, the comparative normalized capacitive plot (as a main parameter for membrane biological state) revealed that 2.1 nano-moles per liter ABZ induced 70% variations in the capacitance of the sensor.

Figure 12B:
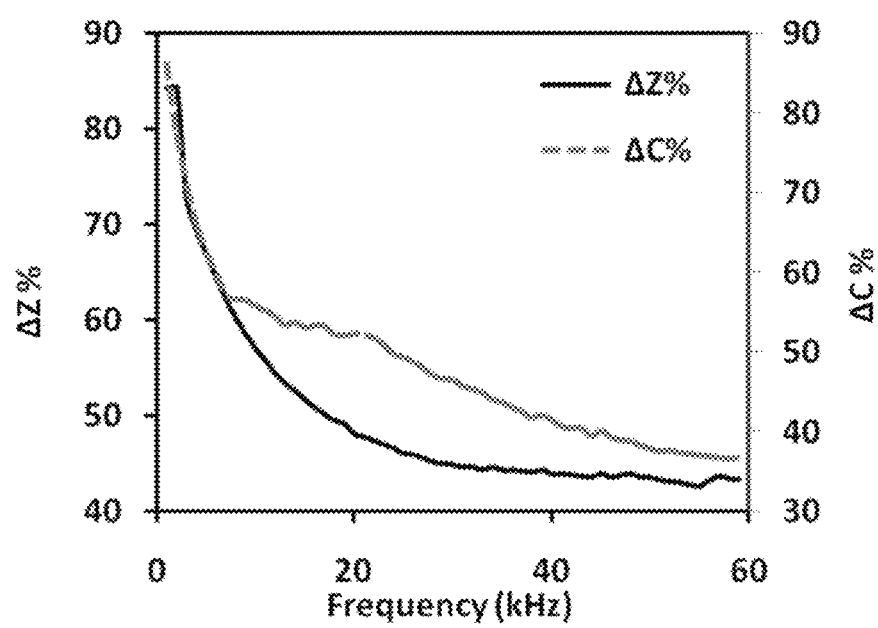
FIG. 12B illustrates the normalized diagram of impedance and capacitance changes for MCF-7 cells seeded on SiNW nano electrodes 2 hours (T1) after treating by 0.1 nanomoles per liter of Paclitaxel (PTX) versus the control sample.

Referring to FIG. 12B, considerable changes in electrical parameters of the cells are also observed after a treatment with 0.1 nano-moles per liter of PTX. Such variations are about 50% in mean impedance of the sensor and about 60% in mean capacitance of the sensor for 2 hours after treatment.

According to the method described in the present example, the samples were maintained in an incubator so that the signal extraction was repeated 10 hours after cells dropping (6 hours after drug incubation for treated samples) to monitor the time evolution of drug induced MT polymerization/depolymerization on bioelectrical response of the membrane.

Figure 12C:
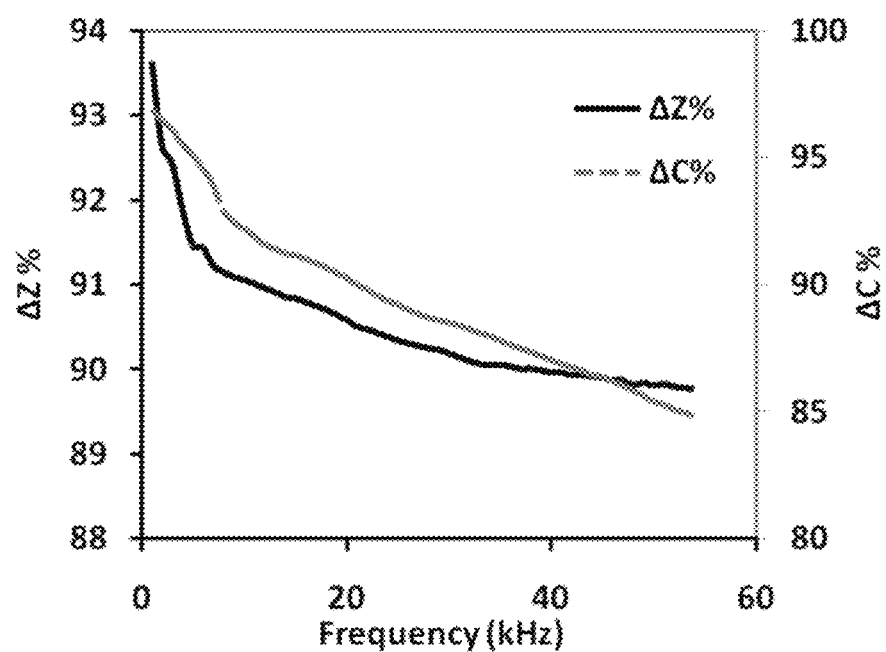
FIG. 12C illustrates the normalized diagram of impedance and capacitance changes for MCF-7 cells seeded on SiNW nano electrodes 6 hours (T2) after treating by 2.1 nanomoles per liter of ABZ versus the control sample.
Figure 12D:
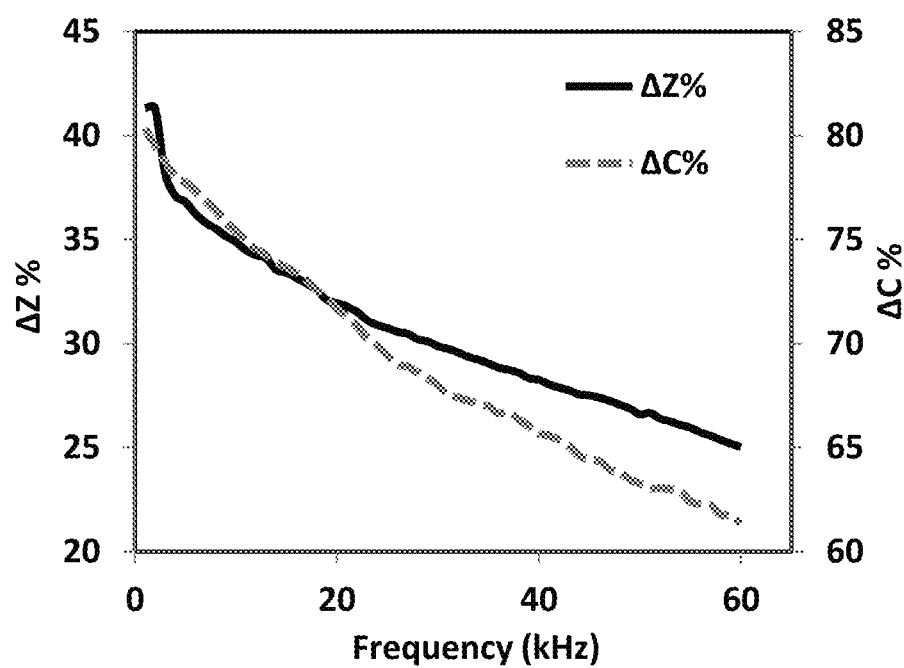
FIG. 12D illustrates the normalized diagram of impedance and capacitance changes for MCF-7 cells seeded on SiNW nano electrodes 6 hours (T2) after treating by 0.1 nano-moles per liter of PTX versus the control sample.

FIGS. 12C and 12D illustrate the comparative electrical responses between control and drug treated samples in which the changes in electrical impedance with respect to control sample is about 90% for ABZ treated sample and about 30% for PTX treated. The norm of capacitive changes in control sample is about 90% more than ABZ and about and 75% more than PTX values. The comparative capacitance is in a well corroboration with impedance.

Figure 12E:
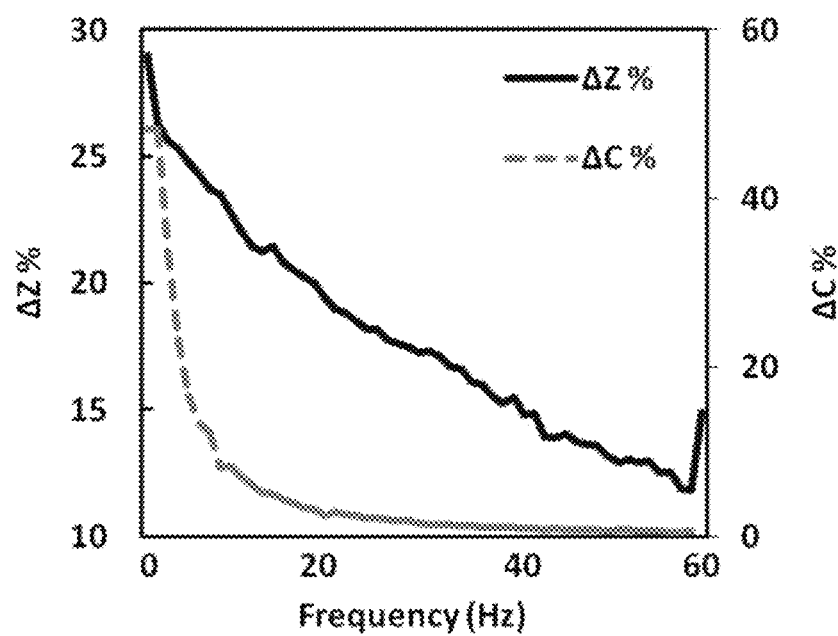
FIG. 12E illustrates the normalized diagram of impedance and capacitance differences for control (untreated) MCF-7 cells seeded on SiNW electrodes between 2 hours (T1) and 6 hours (T2) incubation periods.
Figure 12F:
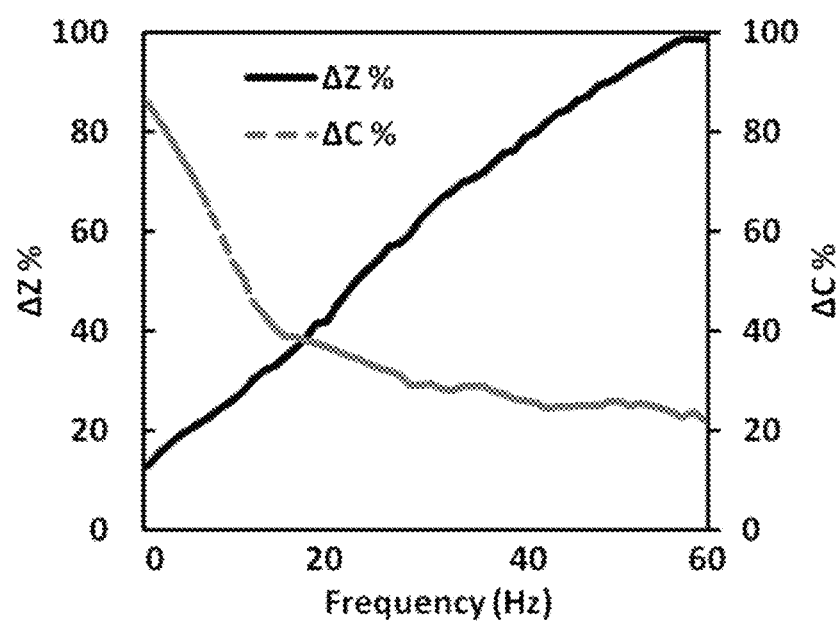
FIG. 12F illustrates the normalized diagram of impedance and capacitance differences for control (untreated) MCF-7 cells seeded on SiNW electrodes between 2 hours (T1) and 6 hours (T2) after treating by 2.1 nano-moles per liter of ABZ.
Figure 12G:
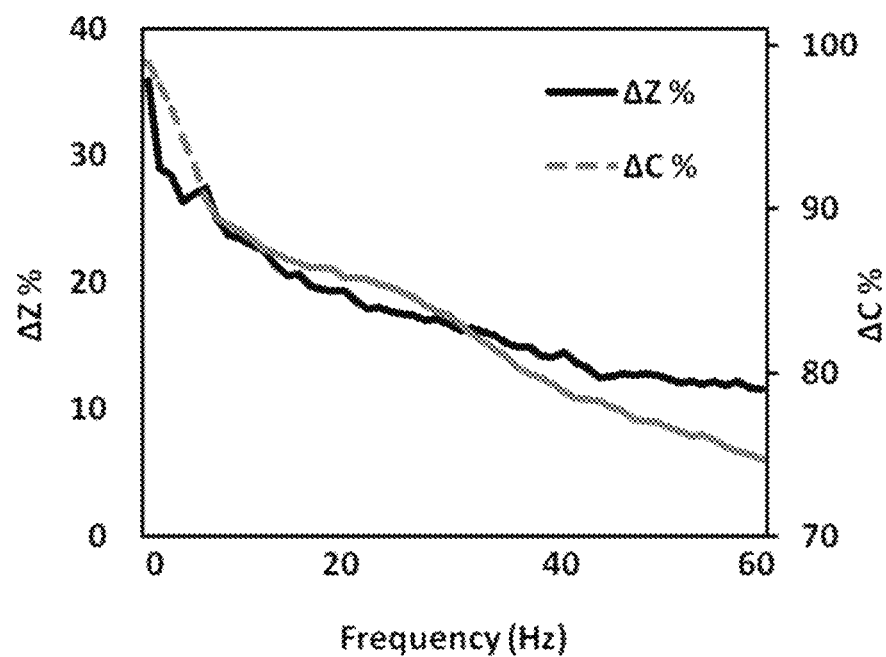
FIG. 12G illustrates the normalized diagram of impedance and capacitance differences for control (untreated) MCF-7 cells seeded on SiNW electrodes between 2 hours (T1) and 6 hours (T2) after treating by 0.1 nano-moles per liter of PTX.

Referring to FIGS. 12E, 12F and 12G, the comparative responses of control sample (FIG. 12E), ABZ treated sample (FIG. 12F) and PTX treated sample (FIG. 12G) after T1 and T2 time intervals are illustrated. It can be observed from these figures that the effect of ABZ is sharper on the bioelectrical impedance of the membrane during time evolution. The norm in impedance of the ABZ treated cells was changed about 60% for 6 hours after drug incubation (ABZT1 vs. ABZT2) meanwhile such variation was 15% in PTX treated cells (PTXT1 vs. PTXT2). But, time dependent variation in capacitive behavior was sharper in PTX treated sample (about 85%).

Accordingly, a mechanism for such variations in electrical impedance can be considered to elaborate the effect of polymerization/depolymerization process in the structure of MTs on bioelectrical properties of the cell membrane whereas its reliability can be investigated by some standard tests such as Confocal, Flowcytometry and tubulin assembly assays. Therefore, a series of confocal images were taken from samples in the present example.

For Confocal imaging, the MCF-7 cells were grown on individual glass slides and treated with ABZ with amount of about 2.1 and 10.5 nano-moles per liter as well as PTX with amount of about 0.1 and 1 nano-moles per liter for 2 hours. In addition, an un-treated control sample was prepared as reference for comparison. Then, samples were washed with PBS and permeabilized with microtubule stabilizing buffer [80 mM PIPES-KOH (pH 6.8), 5 mM EGTA, and 1 mM $MgCl_2$ containing 0.5% Triton X-100] for 5 min at room temperature before being fixed with chilled absolute methanol for 10 min at −20° C. Thereafter, the fixed cells were washed and incubated with monoclonal mouse anti-α-tubulin antibody (Sigma Co.) for 1 hour at room temperature followed by incubation with FITC-conjugated antimouse IgG antibody (Santa Cruz Biotechnology). The stained cells were mounted with Vectashield (Vector Laboratories, Burlingame, Calif.) and observed by confocal microscopy.

Figure 13A:
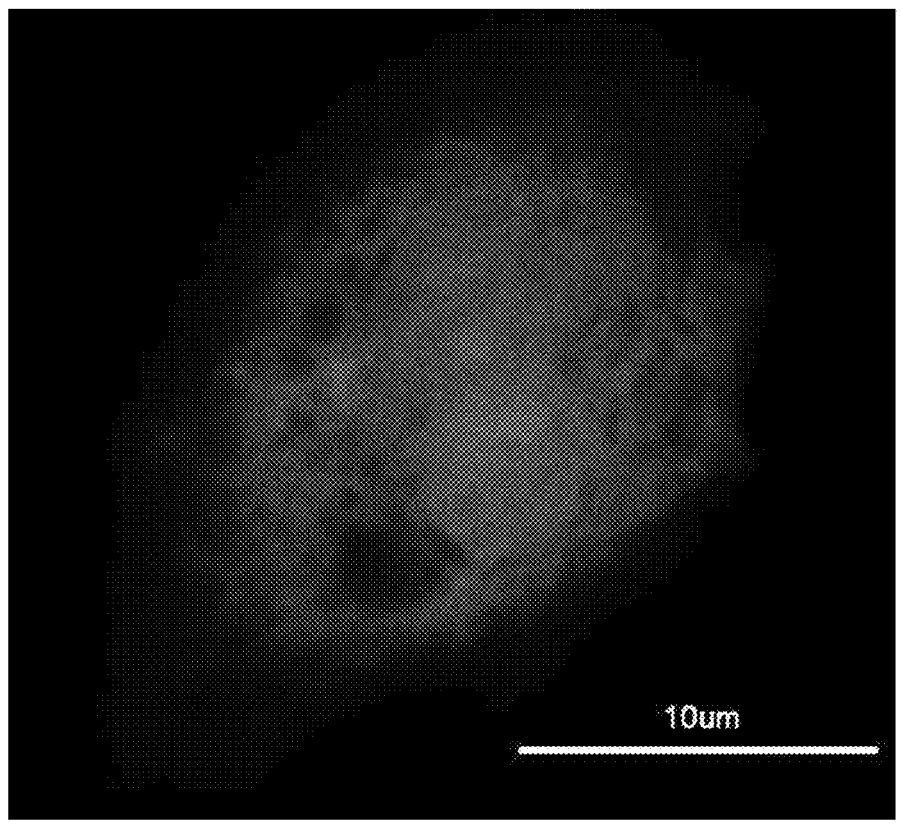
FIG. 13A illustrates a confocal microscopy image from the tubulin assemblies of MCF-7 cells after 2 hours incubation, named as control sample.
Figure 13B:
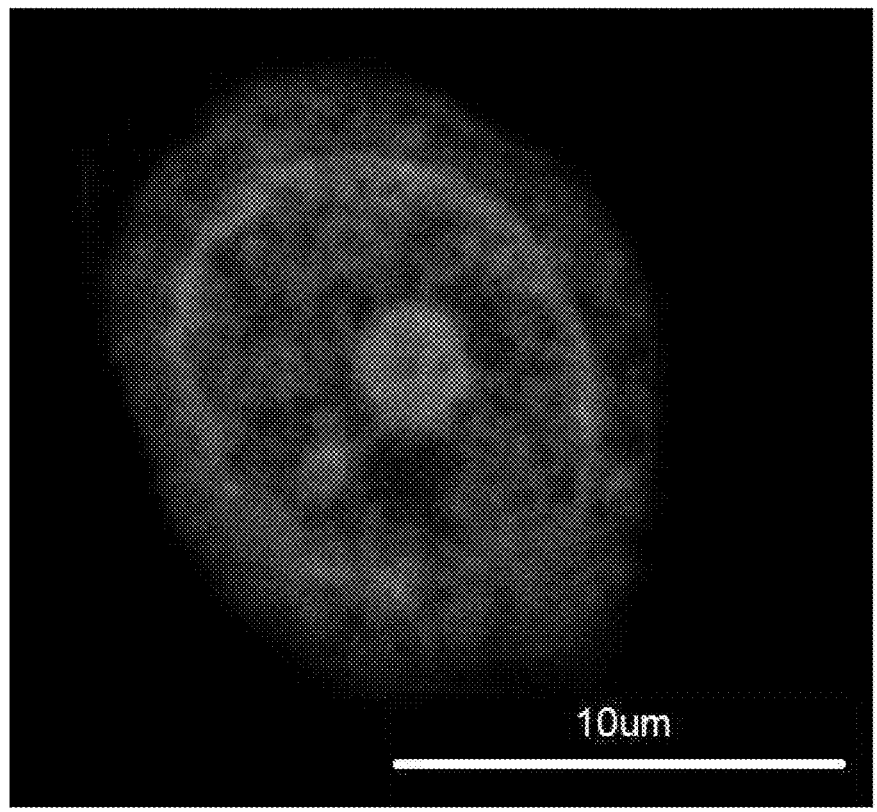
FIG. 13B illustrates a confocal microscopy image from the tubulin assemblies of MCF-7 cells treated with 2.1 nano-moles per liter ABZ after 2 hours incubation.
Figure 13C:
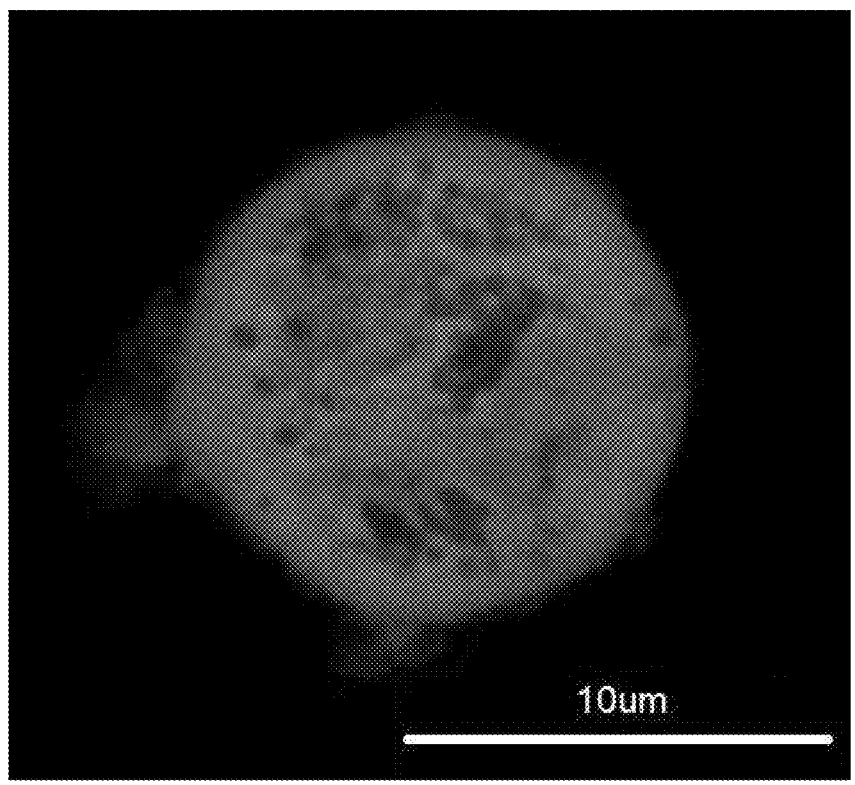
FIG. 13C illustrates a confocal microscopy image from the tubulin assemblies of MCF-7 cells treated with 0.1 nano-moles per liter PTX after 2 hours incubation.

Referring to FIGS. 13A, 13B and 13C, the confocal microscopy images from the tubulin assemblies of MCF-7 cells 2 hours after treatment are illustrated respectively for control (un-treated) sample, treated sample with 2.1 nano-moles per liter ABZ and treated sample with 0.1 nano-moles per liter PTX.

Referring to FIG. 13A, the confocal image taken from untreated cells revealed that normal bipolar spindles are observed in cytoskeletal structure. In contrast, many cells having abnormally reduced numbers of spindles or monopolar (monoaster) spindles for ABZ treated sample as illustrated in FIG. 13B. In contrast, aggregated spindles are observed for PTX treated cells after the same time referring to FIG. 13C.

Figure 14A:
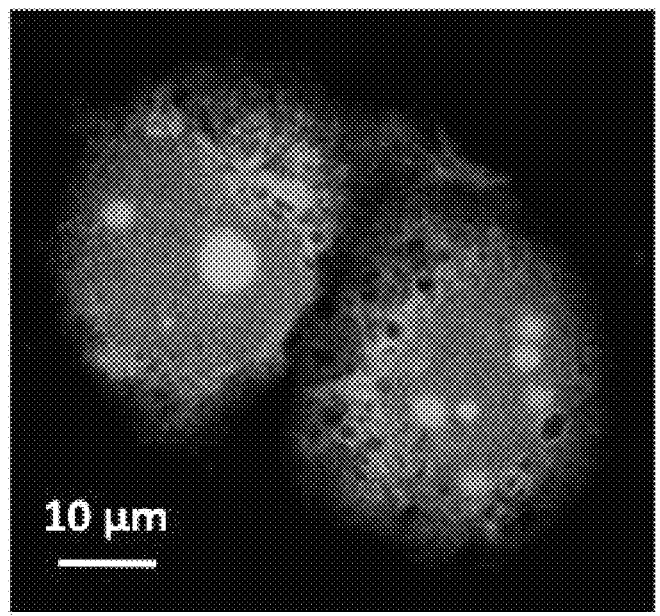
FIG. 14A illustrates a confocal microscopy image from the tubulin assemblies of MCF-7 cells after 6 hours incubation, named as control sample.
Figure 14B:
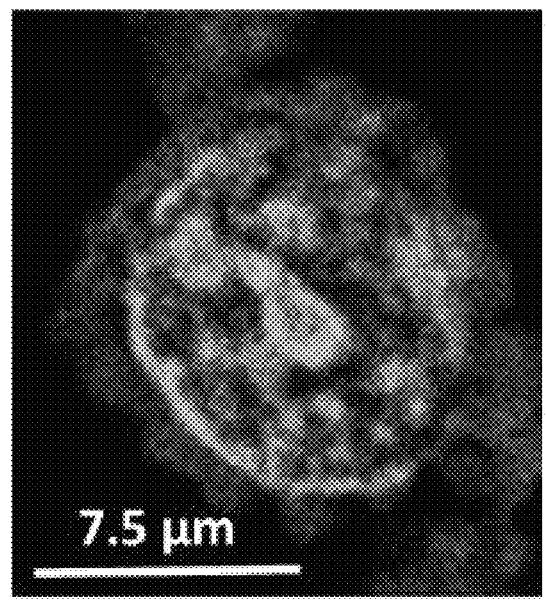
FIG. 14B illustrates a confocal microscopy image from the tubulin assemblies of MCF-7 cells treated with 2.1 nano-moles per liter ABZ after 6 hours incubation.
Figure 14C:
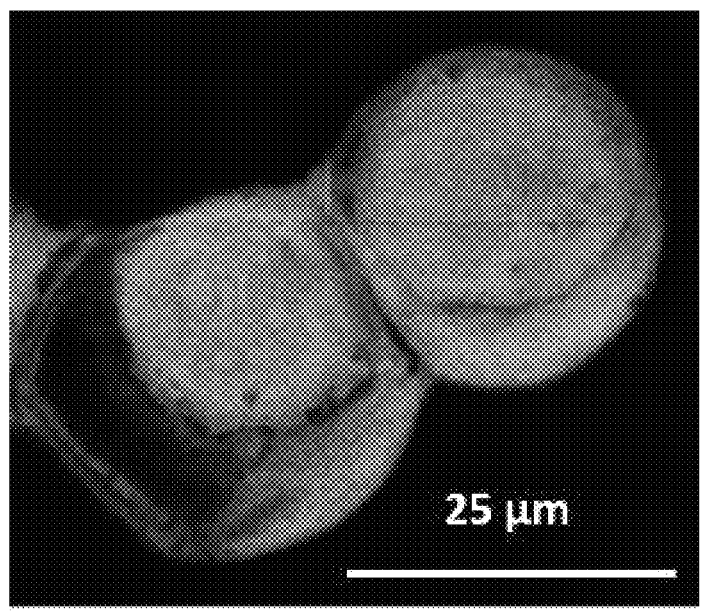
FIG. 14C illustrates a confocal microscopy image from the tubulin assemblies of MCF-7 cells treated with 0.1 nano-moles per liter PTX after 6 hours incubation.

The confocal microscopy images from the tubulin assemblies of MCF-7 cells 6 hours after treatment are illustrated for control sample (FIG. 14A), treated sample with 2.1 nano-moles per liter ABZ (FIG. 14B) and treated sample with 0.1 nano-moles per liter PTX (FIG. 14C).

Referring to FIG. 14B, the spindle inhibitory effects of ABZ is continuously observable 6 hours after drug treatment and still the monoastered MTs are observable in comparison with control sample shown in FIG. 14A. In addition, the increased aggregation in MT spindles is noticeable in PTX treated sample after 6 hours, referring to FIG. 14C.

Hence, the confocal images precisely corroborate the interference of ABZ and PTX on MT assembly in which the perturbation in depolymerization/polymerization rate of MTs affect the normal function of membrane and change the electrical characteristics of the phospholipids and ion channels. ABZ analogues is one class of inhibitors that operates by depolymerization of tubulin to form microtubules and so called polymerization inhibitor. It reduces the mass of microbule polymer in the cells and acts as a microtubule-destabilizing agent (FIGS. 13B and 14B). PTX analogues which is the other class of inhibitors operates by inhibiting the depolymerization of polymerized tubulin and enhances the mass of microtubule polymer in the cells. Therefore, it acts as microbule-stabilizing agent called depolymerization inhibitor (FIGS. 13C and 14C).

Other implementations are contemplated. For example, electrically active nanostructures, such as carbon nanotube, silicon nanowires and nanograsses may be suitable candidates for a well-directed electrical interaction with cell outer-wall to penetrate the electric field into the cell inner parts. Among these, the most important advantage of SiNW-ECIS in addition to the silicon nanowires biocompatibility with biological cells is the direct attachment of biological cells without a need for adhesive layers.

The elasticity and skein architecture of nanowires permit the cells to spread and proliferate on the wires. As can be observed from SEM images, the cells are formed in a 3D shape during proliferation on SiNW arrays. This important ability may allow for great electrical monitoring of cells by 3D electrically activated SiNW electrodes during their growth and mitosis. Additionally, SiNWs could be grown on top of $SiO_2$ layer and then be doped in a doping furnace. Therefore, a good electrical isolation may be achieved between electrodes and substrate.

As such, SiNWs may be more advantages than other electrically active nanostructures. For example, in the case of Si nanograsses, Si nanograsses may have to be fabricated onto the Si substrate by reactive ion etching. Therefore, isolating the electrodes from each other may be complicated and may require multi-step sequential p and n doping to form a reverse bias between the electrodes and substrate. It should be understood by a person skilled in the art that the passivizing quality of the oxide layer is much better than a reverse junction.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various examples for the purpose of streamlining the disclosure. This method of disclosure is not to be interpreted as reflecting an intention that the claims require more features than are expressly recited in each claim. Rather, as the following claims reflect, inventive subject matter lies in less than all features of a single disclosed example. Thus the following claims are hereby incorporated into the Detailed Description, with each claim standing on its own as a separately claimed subject matter.

What is claimed is:

1. A method for detection and monitoring a therapeutic effect of a cancer treatment drug, the method comprising steps of:

providing biological cells;
culturing the biological cells in a controlled set of conditions;
growing a layer of silicon dioxide on a substrate layer;
coating one or more portions of the grown silicon dioxide layer with a catalyst layer, wherein one or more portions of the grown silicon dioxide layer are not coated with the catalyst layer, thereby patterning the catalyst layer to form a sensor region on the substrate layer;
selectively growing a plurality of silicon nanowire electrode arrays on the portions of the silicon dioxide layer that have been coated with the catalyst layer and forming an electrical cell-substrate impedance sensor (ECIS);
seeding the cultured biological cells onto a surface of the grown silicon nanowire electrode arrays such that the biological cells become attached to the silicon nanowire electrode arrays;
adding a cancer treatment drug to the seeded biological cell lines to treat the seeded biological cells, wherein the cancer treatment drug is an antitubulin drug that interferes with proliferation of a cancerous cell and causes cell apoptosis; and
measuring an electrical impedance of the treated biological cells for detection and monitoring of a therapeutic effect of the cancer treatment drug,
wherein adding the treatment drug includes:
adding a specific amount of the treatment drug to the biological cells that are attached to the silicon nanowire electrode arrays, and
maintaining the biological cells with the added treatment drug in an incubator for a specific time interval.

2. The method according to claim 1, wherein the biological cells include cells from epithelial cancerous cell lines supplied from a cell bank or a portion of an epithelial cancerous tumor.

3. The method according to claim 1, wherein the biological cells include cells from breast cancerous cell lines or a portion of a breast cancerous tumor.

4. The method according to claim 2, wherein the epithelial cancerous cell lines include MCF-7 (Michigan Cancer Foundation-7) cell lines.

5. The method according to claim 1, wherein the controlled set of conditions includes maintaining the biological cells in a $CO_2$ incubator.

6. The method according to claim 1, wherein the controlled set of conditions includes maintaining the biological cells at a temperature of about 37° C.

7. The method according to claim 1, wherein the controlled set of conditions includes maintaining the biological cells in a Roswell Park Memorial Institute-1640 (RPMI-1640) medium.

8. The method according to claim 7, wherein the medium is supplemented with a Fetalbovine serum comprising of Fetalbovine with an amount of about 5%.

9. The method according to claim 7, wherein the medium is supplemented with penicillin/streptomycin with an amount of about 1%.

10. The method according to claim 7, wherein the medium is replaced every day with a fresh medium.

11. The method according to claim 1, wherein the ECIS is packed in a plexiglass cover.

12. The method according to claim 1, wherein the ECIS is sealed with a biograde silicon rubber tube.

13. The method according to claim 1, wherein seeding the cultured biological cells includes:

dropping the cultured biological cells on a surface of a packed and sealed ECIS, and maintaining the dropped biological cells in an incubator to achieve attachment between the biological cells and the silicon nanowire electrode arrays of ECIS.

14. The method according to claim 13, wherein the biological cells are trypsinized from a surface of a cell flask or a microwell for less than 4 minutes and at room temperature to detach from the cell flask or the microwell and then are dropped and re-cultured on the silicon nanowire electrode arrays.

15. The method according to claim 13, wherein dropping the cultured biological cells includes dropping the cultured biological cells with a volume of about 300 μl.

16. The method according to claim 13, wherein maintaining the cultured biological cells in the incubator includes maintaining the cultured biological cells in the incubator for about 3 hours to 10 hours.

17. The method according to claim 1, wherein the cancer treatment drug is an antitubulin drug selected from a group consisting of Albendazole (ABZ), Paclitaxel (PTX) or any other antitubulin drug.

18. The method according to claim 17, wherein the ABZ drug has a concentration in a range of about 0.1 to 20 nano-mole per liter.

19. The method according to claim 17, wherein the PTX drug has a concentration in a range of about 0.1 to 20 nano-mole per liter.

20. The method according to claim 1, wherein maintaining the biological cells with the added treatment drug includes maintaining the biological cells with the added treatment drug in the incubator for at least about 2 hours.

21. The method according to claim 1, wherein:

measuring the electrical impedance includes measuring the electrical impedance via a device having a sensor package; a system configured to apply an electrical signal to the sensor package and to acquire an electrical response corresponding to the electrical signal from the sensor package; and a data processor configured to process the electrical response, and the ECIS includes a substrate, a catalyst layer formed on the substrate, and the silicon nanowire electrode arrays grown on the catalyst layer.

22. The method according to claim 21, wherein measuring the electrical impedance includes:

applying a specific voltage to the sensor package having the biological cells attached to the silicon nanowire electrode arrays, and measuring the electrical impedance of the biological cells attached to the silicon nanowire electrode arrays at various specific frequencies.

23. The method according to claim 22, wherein measuring the electrical impedance is performed about 2 hours and 6 hours after the drug treatment.

24. The method according to claim 22, wherein the applied voltage is about 400 mV.

25. The method according to claim 22, wherein the measurement is carried out at a range of frequencies from about 100 Hz to 150 KHz.

26. The method according to claim 1, further comprising patterning and etching the catalyst layer on the grown silicon dioxide layer through a photolithography process.

27. The method according to claim 1, wherein the catalyst layer includes a material of either gold or a bilayer of Ni—Au.

* * * * *